US009023992B2

(12) United States Patent
Rasmussen et al.

(10) Patent No.: US 9,023,992 B2
(45) Date of Patent: May 5, 2015

(54) HYDROPHOBIC INTERACTION CHROMATOGRAPHY PURIFICATION OF FACTOR VII POLYPEPTIDES

(75) Inventors: Daniel E. Rasmussen, København Ø (DK); Janus Krarup, Gentofte (DK)

(73) Assignee: Novo Nordisk Healthcare AG, Zurich (CH)

( * ) Notice: Subject to any disclaimer, the term of this patent is extended or adjusted under 35 U.S.C. 154(b) by 1192 days.

(21) Appl. No.: 12/884,927

(22) Filed: Sep. 17, 2010

(65) Prior Publication Data

US 2011/0064719 A1     Mar. 17, 2011

Related U.S. Application Data

(63) Continuation of application No. 11/514,484, filed on Sep. 1, 2006, now abandoned, which is a continuation-in-part of application No. PCT/EP2005/052024, filed on Nov. 24, 2005.

(60) Provisional application No. 60/577,613, filed on Jun. 7, 2004.

(30) Foreign Application Priority Data

May 4, 2004   (DK) ................................. 2004 00712
Jun. 4, 2004   (DK) ................................. 2004 00882
Sep. 1, 2005  (EP) .................................... 05107990

(51) Int. Cl.
*C07K 14/745*     (2006.01)
*A61K 38/36*     (2006.01)
*A61K 38/48*     (2006.01)

(52) U.S. Cl.
CPC .................................... *C07K 14/745* (2013.01)

(58) Field of Classification Search
CPC . C07K 14/745; A61K 38/36; A61K 38/4846; A61K 38/48
USPC .................. 514/13.5, 13.7, 14.3; 530/381
See application file for complete search history.

(56) References Cited

U.S. PATENT DOCUMENTS

| | | |
|---|---|---|
| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts |
| 4,412,989 A | 11/1983 | Iwashita et al. |
| 4,414,147 A | 11/1983 | Klibanov et al. |
| 4,496,689 A | 1/1985 | Mitra |
| 4,806,595 A | 2/1989 | Noishiki et al. |
| 4,925,796 A | 5/1990 | Bergh et al. |
| 5,154,924 A | 10/1992 | Friden |
| 5,182,107 A | 1/1993 | Friden |
| 5,352,670 A | 10/1994 | Venot et al. |
| 5,374,541 A | 12/1994 | Wong et al. |
| 5,405,753 A | 4/1995 | Brossmer et al. |
| 5,432,059 A | 7/1995 | Bean et al. |
| 5,527,527 A | 6/1996 | Friden |
| 5,545,553 A | 8/1996 | Gotschlich |
| 5,614,184 A | 3/1997 | Sytkowski et al. |
| 5,621,039 A | 4/1997 | Hallahan et al. |
| 5,672,683 A | 9/1997 | Friden et al. |
| 5,716,812 A | 2/1998 | Withers et al. |
| 5,728,554 A | 3/1998 | Bayer et al. |
| 5,833,988 A | 11/1998 | Friden |
| 5,834,251 A | 11/1998 | Maras et al. |
| 5,876,980 A | 3/1999 | DeFrees et al. |
| 5,922,577 A | 7/1999 | Defrees et al. |
| 5,969,040 A | 10/1999 | Hallahan et al. |
| 5,977,307 A | 11/1999 | Friden et al. |
| 6,013,620 A | 1/2000 | Turecek et al. |
| 6,015,555 A | 1/2000 | Friden |
| 6,030,815 A | 2/2000 | DeFrees et al. |
| 6,037,452 A | 3/2000 | Minamino et al. |
| 6,100,061 A | 8/2000 | Reiter et al. |
| 6,166,183 A | 12/2000 | Ishikawa et al. |
| 6,183,738 B1 | 2/2001 | Clark |
| 6,692,931 B1 | 2/2004 | Reutter et al. |
| 6,777,390 B1 | 8/2004 | Matthiessen et al. |
| 7,338,933 B2 | 3/2008 | DeFrees et al. |
| 2002/0137134 A1 | 9/2002 | Gerngross |
| 2005/0250678 A1 | 11/2005 | DeFrees et al. |

FOREIGN PATENT DOCUMENTS

| | | |
|---|---|---|
| AU | 2004/222625 A1 | 9/2004 |
| DK | PA 200301646 | 11/2003 |
| JP | 2000-302689 | 10/2000 |
| JP | 2001-029095 | 2/2001 |
| JP | 2002-518411 A | 6/2002 |
| JP | 2004-510786 | 4/2004 |

(Continued)

OTHER PUBLICATIONS

Coagulation factor Vlla, from www.drugs.com/cons/coagulation-factor-viia-intravenous.html, pp. 1-6. Accessed Jun. 19, 2014.*
Potassium Chloride Vs. Sodium Chloride, from www.wqpmag.com/potassium-chloride-vs-sodium-chloride, pp. 1-3. Accessed May 16, 2014.*
Naturally Occurring Amino Acids, from www.benjamin-mills.com/chemistry/amino-acids.htm, pp. 1-4. Accessed Apr. 9, 2014.*
Cumming, D., Glycobiology, 1991, vol. 1, No. 2, pp. 115-130.
Declaration of Niels Kristian Klausen Dated Jun. 15, 2011.
Bjoern et al., Journal of Biological Chemistry, 1991, vol. 266, No. 17, pp. 11051-11057.
Grebenau et al., Molecular Immunology, 1992, vol. 29, No. 6, pp. 751-758.
Iino et al., Archives of Biochemistry and Biophysics, 1998, vol. 352, No. 2, pp. 182-192.
Jurlander et al., Seminars in Thrombosis and Hemostasis, 2001, vol. 27, No. 4, pp. 373-383.

(Continued)

*Primary Examiner* — Julie Ha
(74) *Attorney, Agent, or Firm* — Nonna G. Akopyan; Reza Green; Richard W. Bork

(57) ABSTRACT

The invention described herein provides new methods of preparing purified Factor VII polypeptide drug substances in large quantities (industrial scale levels) that are associated with reduced content of product-related impurities (e.g., late eluting peaks) and/or that exhibit a relatively uniform glycosylation pattern.

12 Claims, 11 Drawing Sheets

(56) References Cited

FOREIGN PATENT DOCUMENTS

| | | |
|---|---|---|
| JP | 2009-506764 A | 2/2009 |
| WO | 87/00056 A1 | 1/1987 |
| WO | 87/05330 A1 | 9/1987 |
| WO | 89/10134 A1 | 11/1989 |
| WO | 90/07572 A1 | 7/1990 |
| WO | 92/18135 A1 | 10/1992 |
| WO | 94/05332 A2 | 3/1994 |
| WO | 94/15625 A1 | 7/1994 |
| WO | 95/02421 A1 | 1/1995 |
| WO | WO95/18232 | 7/1995 |
| WO | WO96/07753 | 3/1996 |
| WO | 96/32491 A1 | 10/1996 |
| WO | 96/40731 A1 | 12/1996 |
| WO | 98/31826 A1 | 7/1998 |
| WO | 98/58964 A1 | 12/1998 |
| WO | 99/00150 A2 | 1/1999 |
| WO | 99/22764 A1 | 5/1999 |
| WO | WO99/66031 | 12/1999 |
| WO | 00/72873 | 12/2000 |
| WO | 01/49830 A2 | 7/2001 |
| WO | 01/60411 A1 | 8/2001 |
| WO | 01/82943 A2 | 11/2001 |
| WO | WO01/88117 | 11/2001 |
| WO | 02/02597 A2 | 1/2002 |
| WO | 02/13843 A2 | 2/2002 |
| WO | 02/13873 A2 | 2/2002 |
| WO | 02/17957 | 3/2002 |
| WO | 02/29025 A2 | 4/2002 |
| WO | 02/074806 A2 | 9/2002 |
| WO | 03/002524 A2 | 1/2003 |
| WO | 03/031464 A2 | 4/2003 |
| WO | WO 03/046150 | 6/2003 |
| WO | 03/055511 A1 | 7/2003 |
| WO | 03/055512 A1 | 7/2003 |
| WO | 2004/000366 A1 | 12/2003 |
| WO | 2004/082708 A2 | 9/2004 |
| WO | 2004/110469 A2 | 12/2004 |
| WO | WO 2005/014035 | 2/2005 |
| WO | 2005-111225 A1 | 11/2005 |

OTHER PUBLICATIONS

Klausen et al., Molecular Biotechnology, 1998, vol. 9, pp. 195-204.
Klausen et al., Journal of Chromatography, 1995, vol. 718, No. 1, pp. 195-202.
Shao et al., Glycobiology, 2002, vol. 12, No. 11, pp. 763-770.
Thim et al., Biochemistry, 1988, vol. 27, pp. 7785-7793.
Nishimura et al., Journal of Biological Chemistry, 1989, vol. 264, No. 34, pp. 20320-20325.
English language abstract of JP 2001-029095.
Burton SC, Harding DRK, Hydrophobic Charge Induction Chromatography: Salt Independent Protein Adsorpotion and Facile Elution With Aqueous Buffers, Journal of Chromatography A, 1998, 814: 71-81.
Mollerup et al., Biotechnology and Bioengineering, 1995, vol. 48, pp. 501-505.
Bjoern et al., "Human Plasma and Recombinant Factor VII," The Journal of Biological Chemistry, vol. 266, No. 17, Issue of Jun. 15, pp. 11051-11057, 1991.
Daniel Rasmussen, 2007 HIC-RPC Conference (Mar. 2007—Interlaken, Switzerland).
Machine Translation of WO9966031, pp. 1-4, Accessed Mar. 4, 2009.
Hayakawa, "Scienc of Evaluating the Quality and Safety of Biotechnological Products", PDA Journal of GMP Validation in Japan, 2001, vol. 3, No. 2, pp. 57-66.
Kawasaki, "Mass Spectrometric Analysis of Glycoprotein", Summary of Symposia of Annual Meeting of Pharma Society, 2004, vol. 124, No. 1, p. 111.
Ohta et al., "Usefulness of LC/MS as Equality and Homogeneity of Glycoprotein Product", Summaries of Symposia of the Annual Meeting of the Pharmaceutical Society of Japan, Mar. 5, 2001, vol. 121, No. 4, p. 137.
Bolt, Gert et al., Glycobiology, Posttranslational N-Glycosylation Takes Place During the Normal Processing of Human Coagulation Factor VII, 2005, vol. 15 Part 5 pp. 541-547.
Cooper, Ha et al,. Journal of Clinical Investigation, Effects of Thrombin Treatment of Preparations of . . . 1975 vol. 56 Part 3 pp. 751-760.
Josic, D et al., Journal of Chromatography, Preparation of Vitamin K-Dependent Proteins, Such as . . . 2003, vol. 730 Parts 1-2, pp. 183-197.
Soenderkaer, S, et al., European Journal of Pharmaceutical Sciences, Effects of Sucrose on RFVIIA Aggregation and Methionine Oxidation, 2004 vol. 21 pp. 591-606.
Second Declaration of Nields Kristian Klausen Dated Nov. 6, 2012.
Iwanaga et al., Fibrogen, Thrombosis, Coagulation and Fibronolysis, A New Trisaccharide Sugar Chain Linked to a Serine Residue in the First EGF-Like Domain of Clotting Factors VII and IX and Protein Z, 2012 pp. 121-131.
Hollister et al 2001 Glycobiology vol. 11 pp. 1-19.
Hounsell et al. 1996 Glycoconj J vol. 13 pp. 19-26.
Huang et al 1984 Proc Natl Acad Sci USA vol. 81 pp. 2708-2712.
Ichikawa et al. 1992 J Am Chem Soc vol. 114 pp. 9283-9298.
Inoue et al. 1995 Biotechnology Annual Review vol. 1 pp. 297-313.
Ito et al. 1993 Pure Appl Chem Soc vol. 114 pp. 9283-9298.
Jackson et al 1987 Anal Biochem vol. 165 pp. 114-127.
Jarvis et al. 1998 Curr Opin Biotechnol vol. 9 pp. 528-533.
Joppich et al 1979 Markromol Chem vol. 180 pp. 1381-1384.
Joshi et al 1990 J biol Chem vol. 265 pp. 14518-14525.
Jung et al 1983 Biochem Biophys Acta vol. 761 pp. 152-162.
Kalsner et al 1995 Clycoconj J vol. 12 pp. 360-370.
Kasina et al 1998 Bioconjugate Chem vol. 9 pp. 108-117.
Katre et al 1987 Proc Natl Acad Sci USA vol. 84 pp. 1487-1491.
Keppler et al 2001 Glycobiology vol. 11 pp. 11R-18R.
Kitamura et al 1990 Biochem Biophysi Res Commun vol. 28 pp. 1387-1394.
Kitamura et al 1991 Cancer Res vol. 51 pp. 4310-4315.
Kodama et al 1993 Tetrahedron Lett vol. 34 pp. 6419-6422.
Koeller et al 2000 Nature Biotechnology vol. 18 pp. 835-841.
Koide et al 1983 Biochem Biophys Res Commun vol. 111 pp. 659-667.
Kreitmann 2001 Current Pharmaceutical Biotechnology vol. 2 pp. 313-325.
Lai et al 1986 J Biol Chem vol. 261 pp. 3116-3121.
Lee et al 1989 Biochemistry vol. 28 pp. 1856-1861.
Li et al 2002 Trends in Pharmcological Sciences vol. 23 pp. 206-209.
Li et al 2002 Medicinal Research Reviews vol. 22 pp. 225-250.
Lord et al 2001 Clin Cancer Res vol. 7 pp. 2085-2090.
Lougheed et al 1999 J Biol Chem vol. 274 pp. 37717-37722.
Lucklow et al 1993 Curr Opin Biotechnol vol. 4 pp. 564-572.
Liu et al 1996 Chem Eur J vol. 2 pp. 1359-1362.
Lund et al 1995 FASEB J vol. 9 pp. 115-119.
Lund et al 1996 J Immunol vol. 157 pp. 225-263.
Mahal et al 1997 Science vol. 276 pp. 1125-1128.
Maras et al 2000 J Biotechnol vol. 77 pp. 255-263.
Miller et al 1993 Curr Opin Genet Dev vol. 3 pp. 97-101.
Min et al 1996 Endocr vol. 43 pp. 585-593.
Mistry et al 1996 Lancet vol. 348 pp. 1555-1559.
Morimoto et al 1996 Glycoconjugate J vol. 13 pp. 1013-1020.
Nilsson et al. 1984 Methonds Enzymol vol. 104 pp. 56-69.
O'Connell et al 1992 J Biol Chem vol. 267 pp. 25010-25018.
Olson et al 1999 J Biological Chem vol. 274 pp. 29889-29896.
Palacpac et al. 1999 PNAS USA vol. 96 pp. 4692-4697.
Park et al 1986 J Biol Chem vol. 261 pp. 205-210.
Paulson et al 1997 J Biol Chem vol. 252 pp. 8624-8628.
PEG Glucocerebrosidase, Internet Page from www.gaucher.org.uk/peg2.prg printed Jun. 21, 2002.
Zalipsky et al 1992 Chemistry: Biotechnical and Biomedical Applications, Plenum Press, New York.
Pyatak et al 1980 Res Commun Chem Pathol Pharmacol vol. 29 pp. 113-127.
Rambouille et al 1999 J Cell Biol vol. 112 pp. 3319-3330.
Reff et al 2002 Cancer Control vol. 9 pp. 152-166.
Sadler et al 1982 Methods in Enxymology vol. 83 pp. 458-514.
Saneyoshi et al 2001 Biology of Reproduction vol. 65 pp. 1686-1690.
Saxon et al 2000 Science vol. 287 pp. 2007-2010.

(56) References Cited

OTHER PUBLICATIONS

Schwientek et al 1994 Gene vol. 145 pp. 299-303.
Scouten 1987 Methonds in Enzymology vol. 135 pp. 30-65.
Shah et al 1996 J Pharm Scr vol. 85 pp. 1306-1311.
Singh et al 1996 Chem Commun vol. 8 pp. 993-994.
Song et al 2002 J Pharmcol Exp Ther vol. 301 pp. 605-610.
Srinivaschar et al 1989 Biochemistry vol. 28 pp. 2501-2509.
Takane et al 2000 J Pharmacology and Experimental Therapeutics vol. 294 pp. 746-752.
Takeda et al 1995 Trends Biochem Sci vol. 20 pp. 367-371.
Tanner et al 1987 Biochem Biophys Acta vol. 906 pp. 81-91.
Taylor et al 1991 Protein Immobilization Fundamentals and Applications Manual.
Thotakura et al 1987 Meth Enzymol vol. 138 pp. 350-359.
Tsuboi et al 2000 Archives of Biochemistry and Biophysics vol. 374 pp. 100-106.
Udenfriend et al 1995 Ann Rev Biochem vol. 64 pp. 593-591.
Ulloa-Aguirre et al 1999 Endocruine J vol. 11 pp. 205-215.
Uludag et al 2002 Biotechnol Pro vol. 18 pp. 604-611.
Urdal et al 1984 J Chromatog vol. 296 pp. 171-179.
Van Berkel et al 1996 Biochem J vol. 319 pp. 117-122.
Veronese et al 1985 Appl Biochem Biotech vol. 11 pp. 141-152.
Vocadlo et al 2000 in Carbohydrate Chemistry and Biology vol. 2.
Vyas et al 2001 Crit Rev Ther Drug Carrier Syst vol. 18 pp. 1-76.
Wang et al 1996 Tetrahedron Lett vol. 37 pp. 1975-1978.
Welhoner et al 1991 J Biol Chem vol. 226 pp. 4309-4314.
Witte K et al 1997 J Am Chem Soc vol. 119 pp. 2114-2118.
Woghiren et al 1993 Bioconjugate Chem vol. 4 pp. 314-318.
Wong et al 1982 J Org Chem vol. 47 pp. 5416-5418.
Wong et al 1992 Enzyme Microb Technol vol. 14 pp. 866-874.
Woods et al 1989 Eur J Cell Biol vol. 50 pp. 132-143.
Wright et al 1998 J Immunol vol. 160 pp. 3393-3402.
Wu et al 2002 J Druf Targeting vol. 10 pp. 239-245.
Xing et al 1998 Biochem J vol. 336 pp. 667-673.
Yamamoto et al 1998 Carbohydr Res vol. 305 pp. 415-422.
Yarema et al 1998 J Biol Chem vol. 47 pp. 31168-31179.
Yoshida et al 1999 Glycobiology vol. 9 pp. 53-58.
Zalipsku 1995 Bioconjugate Chem vol. 6 pp. 150-165.
English language abstract of Japanese 2001-029095.
Sichler et al. "Crystal Structres of Uninhibited Factor VIIa Link its Cofactor and Substrate-assisted Activation to Specific Interactions"Journal of Molecular Biology (2002) vol. 322(20): 591-603.
BeneFIX. www.benefix.com Accessed May 28, 2014.
Merchref et al. "Structural Investigations of Glycoconjugates at High Sensitivity" Chem Rev. 2002 vol. 102: 321-369.
Li, YuCai et al. "Separation of mistletoe lectins based on the degree of glycosylation using boronate affinity chromatography" J. Chromat (2001) vol. 925: 115-121.
Yousefi, S et al. "Increased UDP-GlcNAc:Gal@1-3GalNAc-R (GlcNAc to GalNAc) ,8-1,6-N-Acetylglucosaminyltransferase Activity in Metastatic Murine Tumor Cell Lines" J Biol Chem vol. 266: 1772-1782 (1991).
Nicolaisen et al. "FVIIa derivatives obtained by autolytic and controlled cathepsin G mediated cleavage" FEBS Letter 1993 vol. 317(3): 245-9.
Declaration by Janus Karup dated Dec. 22, 2008.
Coagulation factor VIa, from www.drugs.com/cons/coagulation-factor-viia-intravenous.html, pp. 1-6. Accessed Jun. 19, 2014.
Gross, HJ. "Florescent CMP-sialic acids as a tool to study the specificty of the CMP-sialic acid carrier and the glycoconjugate sialylation in pernetilized cells." Eur J Biochem. Jan. 15, 1992 203(1-2) pp. 269-275.
Abuchowski et al 1977. J Biol Chem 252: pp. 3578-3586.
Abuchowiski et al. 1984 Cancer Biochem Biophys. vol. 7 pp. 175-186.
Ailor et al. 1999, Glycobiology vol. 10. pp. 837-847.
Altmann et al. 1999, Glycoconjugate J vol. 16. pp. 109-123.
Aplin et al. 1981 CRC Crit Rev Biochem. vol. 131 pp. 25-33.
Beauchamp et al. 1983 Anal Biochem. vol. 131 pp. 25-33.
Berger et al. 1988, Blood vol. 71 pp. 1641-1647.
Berg-Fassman et al. 1993. J Biol. Chem vol. 268 pp. 14861-14866.
Bhadra et al. 2002 Pharmazie. vol. 57 pp. 5-29.
Bickel et al. 2001 Adv Drug Deily Rev. vol. 46 pp. 247-279.
Bhatia et al. 1989 Anal Biochem vol. 178 pp. 408-413.
Bijsterbosch et al. 1996 Eur J Biochem. vol. 237 pp. 344-349.
Biome et al. 1995 Endocrinology vol. 136 pp. 2635-2640.
Boissel et al 1993 J Biol Chem. vol. 268 pp. 15983-15993.
Bouizar et al 1986 Eur J Biochem vol. 155 pp. 141-147.
Boyd et al 1995 Mol Immunol vol. 32 pp. 1311-1318.
Browning et al. 1989 J Immunol. vol. 143 pp. 1589-1867.
Buckman et al. 1981 Makromol Chem vol. 182. pp. 1379-1384.
Burns et al. 2002 Blood vol. 99 pp. 4400-4405.
Butnev et al 1998. Biology of Reproduction vol. 58 pp. 458-469.
Byun et al 1992. ASAIO Journal M649-M653.
Casares et al 2001, Nature Biotech vol. 19 pp. 142-147.
Chaffee et al. 1992 J Clin Invest vol. 89 pp. 1643-1651.
Charter et al. 2000. Glycobiology vol. 10. pp. 1049-1056.
Chern et al. 1991, Eur J Biochem vol. 202 pp. 225-229.
Chiba et al 1995, Biochem J vol. 308 pp. 405-409.
Chrisey et al 1996 Nucleic Acids Res vol. 24 pp. 3031-3039.
Conradt et al. 1987 J Bio Chem vol. 262 pp. 14600-14605.
Crout et al 1998, Curr Opin Chem Biol vol. 2 pp. 98-111.
Delgado et al. 1992 Critical Reviews in Therapeutic vol. 9 pp. 249-304.
Delgado et al. 1990 Biotechnol Appl Biochem. vol. 12 pp. 119-128.
Dunn et al 1991. Eds Polymeric Drugs and Drug Delivery Systems. col. 469 American CHemical Society, Washington DC.
Dwek et al. 1995 J Anat vol. 187 pp. 279-292.
Eavarone et al. 2000 J Biomed Mater Res vol. 51 pp. 10-14.
Fibi et al. 1995 Cells Blood vol. 85 vol. 1229-1236.
Fischer et al 1998 Thrombosis Research vol. 89 pp. 147-150.
Flynn et al 2000 Curr Opin Oncol vol. 12 pp. 574-581.
Garnett et al. 2002 Advanced Drug Delivery Reviews vol. 53 pp. 171-216.
Gillis et al. 1988 Behring Inst Mitt. Aug. vol. 83 pp. 1-7.
Grodberg et al. 1993. Eur J Biochem. vol. 218. pp. 597-601.
Hall et al 2001 Methods in Molecular Biology. vol. 166 pp. 139-154.
Hang et al. 2001, J Am Chem Soc vol. 123 pp. 1242-1243.
Harris 1985 Macronol Chem Phys vol. C25. pp. 325-373.
Hellstrom et al 2001 Methond in Molecular Biology vol. 166 pp. 3-16.
Hermanson et al 1993 Immobilized Affinity Ligand Techniques, Academic Press.
Hermanson 1996 Bioconjugate Techniques, Academic Press, San Diego.
Hilles et al. 2002 American Biotechnology Laboratory Pgs vol. 20 p. 30.
Authors: Bajaj P. S. et al., Title: Isolation and Characterization of Human Factor VII Activation of Factor VII by Factor Xa, Journal: The Journal of Biological Chemistry, Year: 1981, vol. 256, No. 1, pp. 253-259.

* cited by examiner

US 9,023,992 B2

HYDROPHOBIC INTERACTION CHROMATOGRAPHY PURIFICATION OF FACTOR VII POLYPEPTIDES

CROSS-REFERENCE TO RELATED PATENT APPLICATIONS

This application is a continuation of U.S. application Ser. No. 11/514,484, filed Sep. 1, 2006 (PENDING) which is a continuation-in-part of currently copending International Patent Application PCT/EP2005/052024 (published as WO 2005/111225), filed Nov. 24, 2005, which designates the US, and claims the benefit of U.S. Provisional Patent Applications 60/713,429 and 60/577,613, filed Sep. 1, 2005 and Jun. 7, 2004, respectively; European Patent Application 05107990.3, filed Sep. 1, 2005; and Danish Patent Applications PA 2004 00712 and PA 2004 00882, filed May 4, 2004 and Jun. 4, 2004, respectively, the entirety of each of which being hereby incorporated by reference.

FIELD OF THE INVENTION

This invention relates to, i.a., chromatographic methods for purifying Factor VII polypeptides, compositions produced through such purification methods, and uses of such compositions.

BACKGROUND OF THE INVENTION

Factor VII and related polypeptides have been demonstrated to be useful therapeutic agents. Accordingly, there is an increasing need for formulations comprising these proteins that are pharmaceutically acceptable and exhibit a uniform and predetermined clinical efficacy.

The overall industrial-scale process for the purification of a Factor VII polypeptide drug substance may suffer from the drawback that an initial drug substance considerable amount of product-related (Factor VII-related) impurities (such as impurities contained in late eluting peaks (including, e.g., glyco-variants with differing levels of N-linked glycosylation ("des-N-glycan forms")), oxidized forms, proteolytically degraded forms (heavy-chain cleaved forms), or aggregates having a higher molecular weight than the Factor VII polypeptide of interest)).

The article "Amino Acid Sequence and Posttranslational Modifications of Human Factor VIIa from Plasma and Transfected Baby Hamster Kidney Cells", Biochemistry, 1988 Oct. 4; 27(20):7785-93, reports that some heavy chain degradation products co-purify with intact activated Factor VII.

The article "FVIIa Derivatives Obtained by Autolytic and Controlled Cathepsin G Mediated Cleavage", FEBS Lett. 1993 Feb. 15; 317(3):245-9, states that heavy chain cleaved forms of Factor VII cannot be isolated from Factor VII under non-denaturing conditions.

U.S. Pat. No. 6,777,390 (Baxter) concerns purification of factor VII from cryosupernatant by anion exchange and subsequent hydrophobic chromatography on Phenyl-Sepharose.

A problem that also or alternatively may be associated with the preparation of such polypeptides is that the polypeptide may not have a uniform glycosylation pattern.

There remains a need for Factor VII Polypeptide preparations, having reduced amounts of product-related impurities (e.g., Factor VII Polypeptide drug substances that are free or at least substantially free of late eluting peaks) and/or a uniform glycosylation pattern, and methods for making such preparations, particularly in industrial scale quantities. The invention described herein provides new methods for preparing such compositions. This and other advantages and further aspects and features of the invention will be apparent from the description of the invention provided here.

BRIEF DESCRIPTION OF THE INVENTION

The invention described herein provides new methods of preparing Factor VII polypeptide compositions ("purified drug substances"), by application of hydrophobic interaction chromatography (HIC), particularly in large quantities (industrial scale levels), so as to obtain purified drug substances that may be characterized by a reduced content of product-related impurities and/or that exhibit a relatively uniform glycosylation pattern as compared to unpurified starting drug substance.

In one aspect, the inventive process is used to prepare purified drug substance having a reduced content of product-related impurities. This inventive process typically utilizes a hydrophobic interaction chromatography material and a salt or a zwitterion, or a combination of both, in a specified concentration. The inventors have discovered that by following a particular hydrophobic interaction chromatography procedure wherein a salt and/or a zwitterion is used, it is possible to reduce, or virtually eliminate, the presence of late elution peaks in the drug substance.

In a more particular exemplary aspect, the invention provides a process for reducing the content of product-related impurities (e.g., late eluting peaks) in a drug substance of a FVII polypeptide comprising (a) contacting the drug substance with a hydrophobic interaction chromatography material under conditions which facilitate binding of a portion of said drug substance to said hydrophobic interaction chromatography material, said drug substance comprising a salt and/or a zwitterion (i) in a concentration of about 0.1 M or less or (ii) in the range of 0.5 M to 85% of the saturation concentration for the respective salt; (b) optionally washing said hydrophobic interaction chromatography material with a washing buffer; (c) eluting said hydrophobic interaction chromatography material with an elution buffer; and (d) collecting a purified drug substance of the Factor VII polypeptide as an eluate; whereby the content of product-related impurities (e.g., late eluting peaks) (e.g., as determined by methods defined herein) is reduced at least about 50%.

In another exemplary aspect, the invention provides a method of preparing a Factor VII glycoprotein with a substantially uniform glycosylation pattern from a sample of Factor VII glycoprotein with a heterogenic glycopattern using hydrophobic interaction chromatography.

These aspects of the invention are further described in, and additional aspects and features of the invention will be apparent from, the description of the invention provided elsewhere herein.

DETAILED DESCRIPTION OF THE INVENTION

Figure 1:
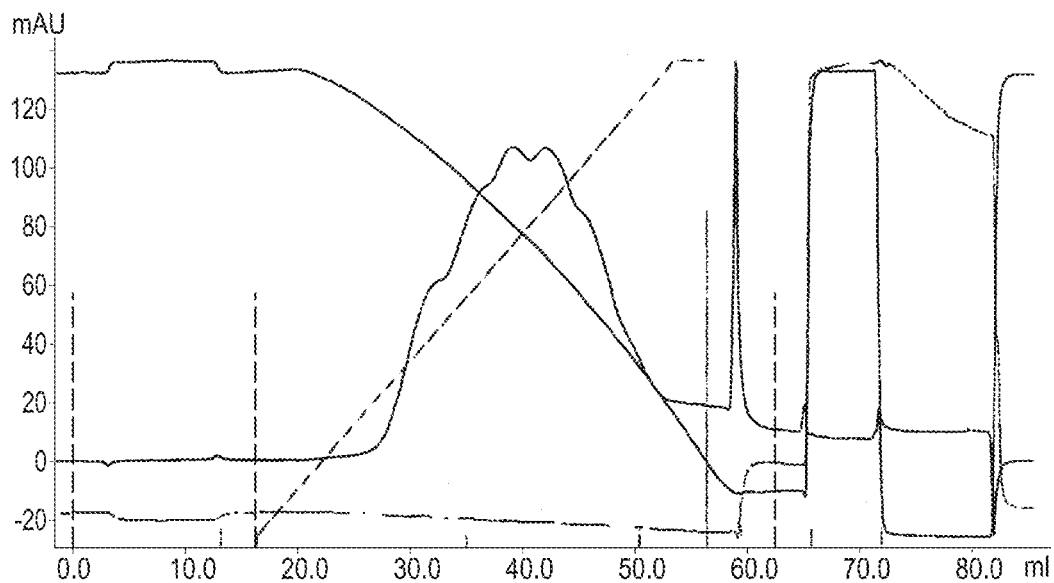
FIG. 1 is a chromatogram of rhFVII separation on TSK-Gel phenyl 5PW, cf. Example 1.

As mentioned above, the invention described herein provides new methods of preparing purified Factor VII polypeptide drug substances in large quantities (industrial scale levels) that are associated with reduced content of product-related impurities and/or that exhibit a relatively uniform glycosylation pattern by application of hydrophobic interaction chromatography.

In one particular exemplary aspect, the invention provides a process for the reduction of product-related impurities in a drug substance of a Factor VII polypeptide (i.e., a composition comprising a Factor VII polypeptide), using hydrophobic interaction chromatography.

A "drug substance" can be either in solid, liquid, or mixed form, e.g. a solution or suspension comprising the Factor VII polypeptide. The expression "drug substance" is in particular meant to refer to a "large" volume or mass, i.e. referring to volumes and masses known from large-scale and industrial-scale processes.

Such purification processes of the invention can be advantageously used to purify Factor VII polypeptide drug substances that initially (i.e., prior to application of the inventive HIC purification technique) have a significant amount of product-related impurities, such as late eluting peaks (at least about 2% of the total amount of Factor VII polypeptides). It should be understood that, in some instances, industrial-scale drug substances of Factor VII polypeptides may include even higher amounts of late eluting peaks, e.g. at least 3%, such as at least 4%, or at least 5%, some times up to about 10%, of late eluting peaks, and that such processes of the present invention may even more relevant for such drug substances. Such drug substances may be obtained directly from fermentation processes, but more usually as the result of initial crude product purification. When used in conjunction with Factor VII polypeptides, the percentage (%) of late eluting peaks is stated as percentage by weight.

Although the exact chemical constitution of high molecular weight impurities remains partly unknown, the expression "late eluting peaks" is intended to mean Factor VII polypeptide-related structures having a higher relative retention time than the Factor VII polypeptide of interest, possibly including oxidized forms of Factor VII polypeptides, undesirable glycoforms, dimers, oligomers, and aggregates. For quantification purposes, the relative retention time (RR) for such "late eluting peaks" is typically from 1040 to 1300.

The invention is furthermore relevant for drug substances of Factor VII polypeptides that initially have a considerable content of oxidized forms, proteolytically degraded forms, and/or aggregates (which aggregates may have a higher molecular weight than the Factor VII polypeptide of interest), namely a pool of proteolytically degraded forms of at least about 2% (w/w) of the total amount of Factor VII polypeptides and/or oxidized forms of at least about 1% (w/w) of the total amount of Factor VII polypeptides.

When used in conjunction with Factor VII polypeptides, the percentage (%) of product-related impurities (e.g., late eluting peaks) is stated as a percentage by weight of the total content of protein (product+product-related impurities). Thus, a two-fold reduction of product-related impurities (e.g., late eluting peaks), e.g. from 2% to 1%, constitutes a relative reduction of 50%; a reduction from, e.g., 8% to 2% thus designates a four-fold reduction, i.e. a relative reduction of 75%; and a reduction from 12% to 6% constitutes a two-fold reduction of content of product-related impurities (i.e. 50% reduction) and not a reduction of 6%-points.

The term "product-related impurities" include, without limitation, glycovariants of Factor VII with differing level of N-linked glycosylation (including, e.g., Factor VII polypeptides lacking one or more N-linked glycans e.g., in positions Asn145 and/or Asn322 of human FVII), oxidized forms, proteolytically degraded or other degraded forms (auto-catalyzed degradation of the heavy chain of the molecule) and aggregates having a higher molecular weight than the Factor VII polypeptide of interest (including dimers, oligomers, polymers).

Although the exact chemical constitution of typical late eluting peak-impurities remains partly unknown, the expression "late eluting peaks" is intended to mean Factor VII polypeptide-related structures having a higher relative retention time than the Factor VII polypeptide of interest, possibly including undesirable glycoforms such as forms where the Factor VII polypeptide is lacking one or more (e.g. one or both) N-linked glycans.

The "relative retention" of the "late eluting peaks" (relative to the FVII polypeptide of interest, e.g. rFVIIa) can be determined using a RP-HPLC assay as described in General methods, below.

The content of late eluting peaks in a drug substance of a Factor VII polypeptide can be determined as described in the "Experimentals" section of this document.

Although not necessarily limited thereto, purification processes of the invention can be advantageously applied to purification of "industrial-scale" (or "large-scale") drug substances of a Factor VII polypeptide. The term "industrial-scale" typically refers to methods wherein the volume of liquid Factor VII polypeptide compositions is at least 10 L, such as at least 50 L, e.g. at least 500 L, or at least 5000 L, or where the weight of the product is at least 1 g (dry matter), such as at least 10 g, e.g. at least 50 g, e.g. 1-1000 g.

As used herein, the term "Factor VII polypeptide" encompasses wild-type Factor VII (i.e. a polypeptide having the amino acid sequence disclosed in U.S. Pat. No. 4,784,950), variants thereof, and Factor VII-related polypeptides, Factor VII derivatives, and Factor VII conjugates. This includes FVII variants, Factor VII-related polypeptides, Factor VII derivatives, and Factor VII conjugates exhibiting substantially the same or improved biological activity relative to wild-type human Factor VIIa.

The term "Factor VII" generally is intended to encompass Factor VII polypeptides in their uncleaved (zymogen) form, as well as those that have been proteolytically processed to yield their respective bioactive forms, which may be designated Factor VIIa. For example, Factor VII typically is cleaved between residues 152 and 153 to yield Factor VIIa. Such variants of Factor VII may exhibit different properties relative to human Factor VII, including stability, phospholipid binding, altered specific activity, and the like. "Factor VII" or "Factor VIIa" within the above definition also includes natural allelic variations that may exist and occur from one individual to another. Also, degree and location of glycosylation or other post-translation modifications may vary depending on the chosen host cells and the nature of the host cellular environment.

The term "Factor VII polypeptide" also encompasses polypeptides, including variants, in which the Factor VIIa biological activity has been substantially modified or somewhat reduced relative to the activity of wild-type Factor VIIa, but that typically retain a significant level of amino acid sequence identity to Factor VII, such as at least about 70%, at least about 75%, at least about 80%, at least about 85%, at least about 90%, at least about 93%, at least about 95%, or more (e.g., about 97, 98, or 99% identity). These polypeptides include, without limitation, Factor VII or Factor VIIa into which specific amino acid sequence alterations have been introduced that modify or disrupt the bioactivity of the polypeptide (as exemplified further herein).

The biological activity of Factor VIIa in blood clotting derives from its ability to (i) bind to Tissue Factor (TF) and (ii) catalyze the proteolytic cleavage of Factor IX or Factor X to produce activated Factor IX or X (Factor IXa or Xa, respectively).

For the purposes of the invention, biological activity of Factor VII polypeptides ("Factor VII biological activity") may be quantified by measuring the ability of a preparation to promote blood clotting, cf. Assay 4 described herein. In this assay, biological activity is expressed as the reduction in clotting time relative to a control sample and is converted to "Factor VII units" by comparison with a pooled human serum standard containing 1 unit/mL Factor VII activity. Alternatively, Factor VIIa biological activity may be quantified by (i) measuring the ability of Factor VIIa or a Factor VII-related polypeptide to produce activated Factor X (Factor Xa) in a system comprising TF embedded in a lipid membrane and Factor X. (Persson et al., J. Biol. Chem. 272:19919-19924, 1997); (ii) measuring Factor X hydrolysis in an aqueous system ("In Vitro Proteolysis Assay", see Assay 2 below); (iii) measuring the physical binding of Factor VIIa or a Factor VII-related polypeptide to TF using an instrument based on surface plasmon resonance (Persson, FEBS Letts. 413:359-363, 1997); (iv) measuring hydrolysis of a synthetic substrate by Factor VIIa and/or a Factor VII-related polypeptide ("In Vitro Hydrolysis Assay", see Assay 1 below); or (v) measuring generation of thrombin in a TF-independent in vitro system (see Assay 3 below).

Factor VII variants having substantially the same or improved biological activity relative to wild-type Factor VIIa encompass those variants that exhibit at least about 25%, preferably at least about 50%, more preferably at least about 75% and most preferably at least about 90% of the specific activity of Factor VIIa that has been produced in the same cell type, when tested in one or more of a clotting assay (Assay 4), proteolysis assay (Assay 2), or TF binding assay as described above. Factor VII variants having substantially reduced biological activity relative to wild-type Factor VIIa are those that exhibit less than about 25%, preferably less than about 10%, more preferably less than about 5% and most preferably less than about 1% of the specific activity of wild-type Factor VIIa that has been produced in the same cell type when tested in one or more of a clotting assay (Assay 4), proteolysis assay (Assay 2), or TF binding assay as described above. Factor VII variants having a substantially modified biological activity relative to wild-type Factor VII include, without limitation, Factor VII variants that exhibit TF-independent Factor X proteolytic activity and those that bind TF but do not cleave Factor X.

Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having an amino acid sequence that differs from the sequence of wild-type Factor VII by insertion, deletion, or substitution of one or more amino acids.

Non-limiting examples of Factor VII variants having substantially the same biological activity as wild-type Factor VII include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189; and FVII variants exhibiting increased proteolytic stability as disclosed in WO 02/38162 (Scripps Research Institute); FVII variants having a modified Gla-domain and exhibiting an enhanced membrane binding as disclosed in WO 99/20767 (University of Minnesota); and FVII variants as disclosed in WO 01/58935 (Maxygen ApS).

Non-limiting examples of Factor VII variants having increased biological activity compared to wild-type FVIIa include FVII variants as disclosed in WO 01/83725, WO 02/22776, WO 02/077218, WO 03/27147, WO 03/37932; WO 02/38162 (Scripps Research Institute); and FVIIa variants with enhanced activity as disclosed in JP 2001061479 (Chemo-Sero-Therapeutic Res Inst.).

As used herein, "Factor VII-related polypeptides" encompasses polypeptides, including variants, in which the Factor VIIa biological activity has been substantially modified, such as reduced, relative to the activity of wild-type Factor VIIa. These polypeptides include, without limitation, Factor VII or Factor VIIa into which specific amino acid sequence alterations have been introduced that modify or disrupt the bioactivity of the polypeptide.

The term "Factor VII derivative" as used herein, is intended to designate a FVII polypeptide exhibiting substantially the same or improved biological activity relative to wild-type Factor VII, in which one or more of the amino acids of the parent peptide have been genetically and/or chemically and/or enzymatically modified, e.g. by alkylation, glycosylation, PEGylation, acylation, ester formation or amide formation or the like. This includes but is not limited to PEGylated human Factor VIIa, cysteine-PEGylated human Factor VIIa and variants thereof. Non-limiting examples of Factor VII derivatives includes GlycoPegylated FVII derivatives as disclosed in WO 03/31464 and US Patent applications US 20040043446, US 20040063911, US 20040142856, US 20040137557, and US 20040132640 (Neose Technologies, Inc.); FVII conjugates as disclosed in WO 01/04287, US patent application 20030165996, WO 01/58935, WO 03/93465 (Maxygen ApS) and WO 02/02764, US patent application 20030211094 (University of Minnesota); and FVII variants as disclosed in WO 01/58935, U.S. Pat. No. 6,806,063, US patent application 20030096338 (Maxygen ApS), WO 03/93465 (Maxygen ApS), WO 04/029091 (Maxygen ApS), WO 04/083361 (Maxygen ApS), and WO 04/111242 (Maxygen ApS), as well as in WO 04/108763 (Canadian Blood Services).

The term "increased-" or "improved biological activity" refers to FVII polypeptides with i) substantially the same or increased proteolytic activity compared to recombinant wild type human Factor VIIa or ii) to FVII polypeptides with substantially the same or increased TF binding activity compared to recombinant wild type human Factor VIIa or iii) to FVII polypeptides with substantially the same or increased half life in blood plasma compared to recombinant wild type human Factor VIIa. The term "PEGylated human Factor VIIa" means human Factor VIIa, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

Non-limiting examples of Factor VII variants having substantially reduced or modified biological activity relative to wild-type Factor VII include R152E-FVIIa (Wildgoose et al., Biochem 29:3413-3420, 1990), S344A-FVIIa (Kazama et al., J. Biol. Chem. 270:66-72, 1995), FFR-FVIIa (Hoist et al., Eur. J. Vasc. Endovasc. Surg. 15:515-520, 1998), and Factor VIIa lacking the Gla domain, (Nicolaisen et al., FEBS Letts. 317:245-249, 1993).

Examples of Factor VII polypeptides include, without limitation, wild-type Factor VIII, L305V-FVII, L305V/M306D/D309S-FVII, L3051-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/

V158D-FVII, F374Y/L305V/E296V-FVII, F374Y/L305V/ M298Q-FVII, F374Y/L305V/V158T-FVII, F374Y/L305V/ S314E-FVII, F374Y/K337A/S314E-FVII, F374Y/K337A/ V158T-FVII, F374Y/K337A/M298Q-FVII, F374Y/K337A/ E296V-FVII, F374Y/K337A/V158D-FVII, F374Y/V158D/ S314E-FVII, F374Y/V158D/M298Q-FVII, F374Y/V158D/ E296V-FVII, F374Y/V158T/S314E-FVII, F374Y/V158T/ M298Q-FVII, F374Y/V158T/E296V-FVII, F374Y/E296V/ S314E-FVII, F374Y/S314E/M298Q-FVII, F374Y/E296V/ M298Q-FVII, F374Y/L305V/K337A/V158D-FVII, F374Y/ L305V/K337A/E296V-FVII, F374Y/L305V/K337A/ M298Q-FVII, F374Y/L305V/K337A/V158T-FVII, F374Y/ L305V/K337A/S314E-FVII, F374Y/L305V/V158D/ E296V-FVII, F374Y/L305V/V158D/M298Q-FVII, F374Y/ L305V/V158D/S314E-FVII, F374Y/L305V/E296V/ M298Q-FVII, F374Y/L305V/E296V/V158T-FVII, F374Y/ L305V/E296V/S314E-FVII, F374Y/L305V/M298Q/ V158T-FVII, F374Y/L305V/M298Q/S314E-FVII, F374Y/ L305V/V158T/S314E-FVII, F374Y/K337A/S314E/V158T-FVII, F374Y/K337A/S314E/M298Q-FVII, F374Y/K337A/ S314E/E296V-FVII, F374Y/K337A/S314E/V158D-FVII, F374Y/K337A/V158T/M298Q-FVII, F374Y/K337A/ V158T/E296V-FVII, F374Y/K337A/M298Q/E296V-FVII, F374Y/K337A/M298Q/V158D-FVII, F374Y/K337A/ E296V/V158D-FVII, F374Y/V158D/S314E/M298Q-FVII, F374Y/V158D/S314E/E296V-FVII, F374Y/V158D/ M298Q/E296V-FVII, F374Y/V158T/S314E/E296V-FVII, F374Y/V158T/S314E/M298Q-FVII, F374Y/V158T/ M298Q/E296V-FVII, F374Y/E296V/S314E/M298Q-FVII, F374Y/L305V/M298Q/K337A/S314E-FVII, F374Y/ L305V/E296V/K337A/S314E-FVII, F374Y/E296V/ M298Q/K337A/S314E-FVII, F374Y/L305V/E296V/ M298Q/K337A-FVII, F374Y/L305V/E296V/M298Q/ S314E-FVII, F374Y/V158D/E296V/M298Q/K337A-FVII, F374Y/V158D/E296V/M298Q/S314E-FVII, F374Y/ L305V/V158D/K337A/S314E-FVII, F374Y/V158D/ M298Q/K337A/S314E-FVII, F374Y/V158D/E296V/ K337A/S314E-FVII, F374Y/L305V/V158D/E296V/ M298Q-FVII, F374Y/L305V/V158D/M298Q/K337A-FVII, F374Y/L305V/V158D/E296V/K337A-FVII, F374Y/ L305V/V158D/M298Q/S314E-FVII, F374Y/L305V/ V158D/E296V/S314E-FVII, F374Y/V158T/E296V/ M298Q/K337A-FVII, F374Y/V158T/E296V/M298Q/ S314E-FVII, F374Y/L305V/V158T/K337A/S314E-FVII, F374Y/V158T/M298Q/K337A/S314E-FVII, F374Y/ V158T/E296V/K337A/S314E-FVII, F374Y/L305V/ V158T/E296V/M298Q-FVII, F374Y/L305V/V158T/ M298Q/K337A-FVII, F374Y/L305V/V158T/E296V/ K337A-FVII, F374Y/L305V/V158T/M298Q/S314E-FVII, F374Y/L305V/V158T/E296V/S314E-FVII, F374Y/E296V/ M298Q/K337A/V158T/S314E-FVII, F374Y/V158D/ E296V/M298Q/K337A/S314E-FVII, F374Y/L305V/ V158D/E296V/M298Q/S314E-FVII, F374Y/L305V/ E296V/M298Q/V158T/S314E-FVII, F374Y/L305V/ E296V/M298Q/K337A/V158T-FVII, F374Y/L305V/ E296V/K337A/V158T/S314E-FVII, F374Y/L305V/ M298Q/K337A/V158T/S314E-FVII, F374Y/L305V/ V158D/E296V/M298Q/K337A-FVII, F374Y/L305V/ V158D/E296V/K337A/S314E-FVII, F374Y/L305V/ V158D/M298Q/K337A/S314E-FVII, F374Y/L305V/ E296V/M298Q/K337A/V158T/S314E-FVII, F374Y/ L305V/V158D/E296V/M298Q/K337A/S314E-FVII, S52A-Factor VII, S60A-Factor VII; R152E-Factor VII, S344A-Factor VII, Factor VIIa lacking the Gla domain; and P11Q/K33E-FVII, T106N-FVII, K143N/N145T-FVII, V253N-FVII, R290N/A292T-FVII, G291N-FVII, R315N/ V317T-FVII, K143N/N145T/R315N/V317T-FVII; and FVII having substitutions, additions or deletions in the amino acid sequence from 233Thr to 240Asn, FVII having substitutions, additions or deletions in the amino acid sequence from 304Arg to 329Cys, and FVII having substitutions, deletions, or additions in the amino acid sequence Ile153-Arg223.

Thus, substitution variants in a factor VII polypeptide include, without limitation substitutions in positions P10, K32, L305, M306, D309, L305, L305, F374, V158, M298, V158, E296, K337, M298, M298, S336, S314, K316, K316, F374, S52, S60, R152, S344, T106, K143, N145, V253, R290, A292, G291, R315, V317, and substitutions, additions or deletions in the amino acid sequence from T233 to N240 or from R304 to C329; or from I153 to R223, or combinations thereof, in particular variants such as P10Q, K32E, L305V, M306D, D309S, L3051, L305T, F374P, V158T, M298Q, V158D, E296V, K337A, M298Q, M298K, S336G, S314E, K316H, K316Q, F374Y, S52A, S60A, R152E, S344A, T106N, K143N, N145T, V253N, R290N, A292T, G291N, R315N, V317T, and substitutions, additions or deletions in the amino acid sequence from T233 to N240, or from R304 to C329, or from I153 to R223, or combinations thereof.

In a first step of the HIC product-related impurity removal (purification) processes, a drug substance of a Factor VII polypeptide is contacted with a hydrophobic interaction chromatography material under conditions which facilitate binding of a portion of said drug substance to said hydrophobic interaction chromatography material. The drug substance should comprise a salt and/or a zwitterion in a concentration of in the range of 0.0-0.1 M or in the range of 0.5 M to 85% of the saturation concentration for the respective salt. The aim is to facilitate binding of a portion of said drug substance of the Factor VII polypeptide to said hydrophobic interaction chromatography material. In a particularly preferred embodiment, the drug substance comprises a salt in a concentration of in the range of 0.5 M to 85% of the saturation concentration, e.g. 0.7-2.2 M.

The term "portion" in connection with step (a) of the above-described method means at least 30% (i.e. 30-100%) of the mass of the Factor VII polypeptide present in the drug substance of the Factor VII polypeptide. It should be understood that it in most instances is desirable to bind far more than 30% of the mass of the Factor VII polypeptides, e.g. at least 50%, or at least 70%, or a predominant portion. By the term "predominant portion" is meant at least 90% of the mass of the Factor VII polypeptide present in the drug substance of the Factor VII polypeptide. Preferably an even higher portion becomes bound to the hydrophobic interaction chromatography material, e.g. at least 95% of the mass, or at least 98% of the mass, or at least 99% of the mass, or even substantially all of the mass of the Factor VII polypeptide present in the drug substance of the Factor VII polypeptide.

The drug substance of the Factor VII polypeptide typically originates from an industrial-scale production process, e.g. a cell culture, a microbial process, a cloned animal (e.g. cows, pigs, sheep, goats, and fish) or insect, or the like, in particular from a cell culture.

The hydrophobic interaction chromatography material is a matrix substituted with hydrophobic ligands such as ethyl, butyl, phenyl, or hexyl (which appears to be responsible for binding the protein). Preferred materials are those substituted with butyl and/or phenyl ligands. The material is most often presented in the form of beads, e.g. a particulate material having an average diameter of in the range of 0.1-1000 µm, or in the form of sticks, membranes, pellets, monoliths, etc.

The most common arrangement of the hydrophobic interaction chromatography material is in a column format. Arrangement in a batch container is of course also possible.

The drug substance of the Factor VII polypeptide is typically obtained directly from a preceding purification step, or from a preceding purification step with subsequent adjustment of pH, ionic strength, chelation of divalent metal ions, etc., if desirable or beneficial.

The contacting of the drug substance of the Factor VII polypeptide is typically conducted according to conventional protocols, i.e. the concentration, temperature, ionic strength, etc. of the drug substance may be as usual, and the hydrophobic interaction chromatography material may be washed and equilibrated before application as usual.

The load of Factor VII polypeptide in the above-described HIC method is typically at least 250 mg per liter of matrix (HIC material), such as in the range of about 0.5-10 g, e.g. 2-5 g, Factor VII polypeptide per liter of matrix (hydrophobic interaction chromatography material in wet form), and the drug substance is typically loaded at a flow of 1-50 column volumes per hour.

The pH of the drug substance before and upon application to the hydrophobic interaction chromatography material appears to play a relevant role for the formation of late eluting peaks. Thus, it is preferred that the drug substance is in liquid form and has a pH in the range of about 3-10, such as in the range of about 3-7, or about 6.5-10, upon application to the hydrophobic interaction chromatography material. In some interesting embodiments, the drug substance has a pH of in the range of about 4-7, or in the range of about 7-9, or in the range of 4.5-8.5. A preferred pH range is about 5-6.5.

The content of calcium ions may play a role in connection with the stability of the Factor VII polypeptide. In some preferred embodiments, the drug substance in step (a) has a concentration of calcium ions of at least 5 mM, such as in the range of 5-100 mM. In such instances, a preferred pH range is about 5-9.5

Typically, the conductivity is at least 40 mS/cm, such as at least 50 mS/cm, such as at least 100 mS/cm such at lest 200 mS/cm.

The temperature of the drug substance is typically 0-25° C., such as around 2-10° C. or 2-8° C.

The temperature of the hydrophobic interaction chromatography material with the bound Factor VII polypeptide is typically 0-25° C., such as around 2-10° C. or 2-8° C., e.g. kept within a specified range by using a cooling jacket and solutions of controlled temperature.

In a particular exemplary aspect, the temperature of the HIC material in steps (a)-(c) is in the range of 0-25° C. (e.g., about 2-10° C., such as 2-8° C., for example, 3, 4, 5, 6, or 7° C.), and wherein pH of steps (a)-(c) is in the range of about 6-9 (e.g., 6.5, 7, 7.5, 8, or 8.5).

The expression "salt" used herein is intended to refer to one or more salts capable of making the Factor VII polypeptide so relatively hydrophobic that is will bind to the hydrophobic interaction chromatography material. Preferred examples of salts are those selected from combinations of particular cations and particular anions. The group of cations comprises ammonium, sodium and potassium, and the group of anions comprises sulfate, acetate and chloride. Examples of salts are ammonium acetate, ammonium sulphate, ammonium chloride, sodium chloride, sodium acetate, sodium sulphate, potassium acetate, potassium chloride and potassium sulphate. Preferred salts are ammonium acetate, ammonium sulphate, sodium acetate, and sodium chloride.

The following table states the solubility (saturation) at 20° C. and the molar concentration corresponding to 85% of saturation for a series of useful salts.

| Salt | Molecular weight (g/mol) | Solubility (g/100 g water) | Solubility mol/L | Solubility 85% |
| --- | --- | --- | --- | --- |
| Ammonium acetate | 77.1 | 148.0 | 19.2 | 16.3 |
| Ammonium chloride | 53.5 | 39.5 | 7.4 | 6.3 |
| Ammonium sulfate | 132.1 | 76.4 | 5.8 | 4.9 |
| Calcium acetate | 158.2 | 43.6 | 2.8 | 2.3 |
| Calcium chloride | 110.9 | 81.3 | 7.3 | 6.2 |
| Lithium acetate | 66.0 | 45.0 | 6.8 | 5.8 |
| Lithium chloride | 42.4 | 84.5 | 19.9 | 16.9 |
| Magnesium chloride | 95.2 | 56.0 | 5.9 | 5.0 |
| Manganese(II) chloride | 125.8 | 77.3 | 6.1 | 5.2 |
| Potassium acetate | 98.1 | 269.0 | 27.4 | 23.3 |
| Potassium chloride | 74.6 | 35.5 | 4.8 | 4.0 |
| Potassium phosphate | 212.3 | 106.0 | 5.0 | 4.2 |
| Sodium acetate | 82.0 | 50.4 | 6.1 | 5.2 |
| Sodium chloride | 58.4 | 36.0 | 6.2 | 5.2 |
| Sodium citrate | 294.1 | 72.0 | 2.4 | 2.1 |
| Sodium sulfate | 142.0 | 28.1 | 2.0 | 1.7 |
| Glycine | 75.0 | 22.5 | 3.0 | 2.6 |

Above data at 20° C.

The expression "zwitterion" is intended to mean an ion which carries both a negative and a positive electrical charge, but which forms a neutral molecule. Examples of useful zwitterions are neutral amino acids, e.g. glycine, alanine, beta-alanine, leucine, isoleucine, etc., in particular glycine and beta-alanine.

It will be understood that the saturation concentration of a particular salt (and thereby the concentration which constitutes 85% of the saturation concentration) will vary depending on the actual temperature used, e.g. the saturation concentration will normally be lower at 5° C. compared to that of 20° C. The solubility (saturation) at 20° C. of particular, useful salts are described above. Solubility at 20° C. for other salts as well as solubility at other temperatures (e.g. 5° C.) can be found in general handbooks of chemistry, such as, e.g. The CRC Handbook of Chemistry and Physics (CRC Press). Alternatively, solubility curves for dissolution of a particular solid (salt) in water can easily be obtained by dissolving a known weight of a salt in varying, known volumes of water, and at each concentration allowing the solution to cool to determine at which temperature the salt begins to crystallize out of solution. That is, for a certain weight of salt, the quantity of water is progressively increased, and for each increase the temperature required to reach the point of saturation is determined. The weight of salt and the weight of water for each saturation temperature represent the concentration of a saturated solution for that temperature, and is expressed in terms of g salt per 100 g water. A solubility curve is then drawn by plotting the g salt per 100 g water on y-axis against saturation temperature on x axis. As such, the solubility of a solid may be expressed as the number of moles of solid dissolved in a liter of liquid, or as the mole fraction of the solid, or, as in this experiment, as the number of grams of solid dissolved in 100 mL of liquid.

It is to be understood that the term "the range of 0.5 M to 85% of the saturation concentration for the respective salt" is intended to mean a range from 0.5 M to 85% of the saturation concentration of a particular salt at the actual temperature at which the relevant method step or steps (loading (a), washing (b), elution (c)) is/are carried out.

After binding of the drug substance of the Factor VII polypeptide to the hydrophobic interaction chromatography materials, a washing step (b) is typically conducted in order to remove a substantial fraction of the late eluting peaks from the hydrophobic interaction chromatography material. By this step, the remaining (bound) fraction of the Factor VII polypeptide on the hydrophobic interaction chromatography material will have a much lower abundance of late eluting peaks.

The content of a salt and/or zwitterions in the washing buffer has also turned out to provide certain advantages. Thus, preferably, the washing buffer in step (b) comprises a salt and/or a zwitterion in a concentration of in the range of 0.0-0.1 M or in the range of 0.5 M to 85% of the saturation concentration for the respective salt. Most preferably, the concentration of the salt and/or zwitterions in the washing buffer is within ±0.1 M of the concentration of the salt in the drug substance in step (a). In a particularly preferred embodiment, the washing buffer comprises a salt in a concentration of in the range of 0.5 M to 85% of the saturation concentration, e.g. 0.7-2.2 M.

This washing step (b) in the above-described method is preferably conducted with a washing buffer having a pH in the range of 2.0-6.9. In some interesting embodiments, the washing buffer has a pH in the range of 3.0-10.0, such as in the range of 3.0-7.0, or 6.5-10.0, upon application to the hydrophobic interaction chromatography material. In some interesting embodiments, the washing buffer has a pH of in the range of 4.0-7.0, or in the range of 7.0-9.0, or in the range of 4.5-8.5.

As above in step (a), the presence of calcium ions appears to play a certain role. Thus, the washing buffer in step (b) typically has a concentration of calcium ions of at least 5 mM, such as in the range of 5-100 mM.

The washing step (b) is typically conducted at a flow of 1-50 column volumes per hour.

The washing buffer is typically an aqueous solution comprising a buffering agent, typically a buffering agent comprising at least one component selected from the groups consisting of acids and salts of MES, PIPES, ACES, BES, TES, HEPES, TRIS, histidine, imidazole, glycine, glycylglycine, glycinamide, phosphoric acid, acetic acid (e.g. sodium acetate), lactic acid, glutaric acid, citric acid, tartaric acid, malic acid, maleic acid, and succinic acid. It should be understood that the buffering agent may comprise a mixture of two or more components, wherein the mixture is able to provide a pH value in the specified range. As examples can be mentioned acetic acid and sodium acetate, etc.

It should be understood that the washing step (b) may be conducted by using one, two or several different washing buffers, or by the application of a gradient washing buffer.

It should also be noted that the washing step and the elution step need not to be discrete steps, but may be combined, in particular if a gradient elution buffer is utilized in the elution step.

After the washing step(s) (c), the hydrophobic interaction chromatography material is eluted with an elution buffer, and a purified drug substance of the Factor VII polypeptide is collected as an eluate.

A great deal of variability is possible for the elution step (c). As for the before-mentioned steps, the elution buffer preferably also comprises a salt and/or a zwitterion.

The type of elution is not particularly critical, thus, it is, e.g., possible to elute with a elution buffer comprising a stepwise decreasing gradient of the salt and/or zwitterion, elute with a linear decreasing gradient of the salt (or a gradient-hold-gradient profile, or other variants), or to use a pH gradient, or to us a temperature gradient, or a combination of the before-mentioned. Alternatively, a gradient of a calcium chelating compound (e.g. EDTA, citrate, malonate, etc.) or a solvent less polar than water (e.g. aqueous solutions comprising ethanol, PEG, 2-propanol, or the like), may be used as the elution buffer.

In one embodiment, the elution buffer comprises a salt in an initial concentration of in the range of 0.7-2.2 M.

In one embodiment, the elution buffer does not contain a calcium-chelating compound. In another embodiment, the elution buffer does not contain EDTA and/or citrate. In one embodiment, the elution buffer contains a calcium salt; in another embodiment is does not contain a calcium salt. In one embodiment, the method according to the invention is carried out in the presence of a calcium salt; in another embodiment, the method according to the invention is carried out in the absence of a calcium salt.

Hence, in a currently most preferred embodiment, the elution buffer in step (c) is a gradient buffer with respect to the an ammonium salt, wherein the initial concentration of the ammonium salt of the gradient buffer is in the range of 1.7-2.2 M, and the final concentration of the ammonium salt of the gradient buffer is in the range of 0-1.6 M.

The conductivity of the final elution buffer is preferably lower than the conductivity of the composition comprising the drug substance in step (a).

In most instances, the elution buffer in step (c) typically has a pH as in step (a) and (b).

Also preferred are the embodiments where the elution buffer in step (c) has a concentration of calcium ions of at least 5 mM, such as in the range of 5-100 mM.

The elution step (c) is typically conducted at a flow of 1-50 column volumes per hour.

The term "purified drug substance" means that the resulting drug substance, i.e. the drug substance collected in step (c), has a lower content of late eluting peaks than the drug substance applied in step (a). The term "purification" refers to the process wherein a purified drug substance can be obtained, e.g., the HIC purification method described herein.

Typically, the process of the present invention is capable of reducing the content of product-related impurities, including late eluting peaks, with at least about 50% compared to—or relative to—the initial content of said impurities in the drug substance, however more preferably, and also realistically, the relative reduction is at least 60%, such as at least 70% or even at least 80% or at least 85%.

In one embodiment, the product-related impurities are late eluting peaks. In another embodiment, the product-related impurities are Factor VII polypeptides lacking one or more N-linked glycan(s). In other embodiments, the product-related impurities are oxidized forms, proteolytically degraded forms (auto-catalyzed degradation of the heavy chain of the molecule) or aggregates having a higher molecular weight than the Factor VII polypeptide of interest (including dimers, oligomers, polymers). In another embodiment the product-related impurities contains a mixture of one or more of the above-mentioned forms, peaks and glycan-lacking forms.

Furthermore, it has been found that the process of the invention very efficiently renders it possible to remove product-related impurities, such as late eluting peaks from drug substances of Factor VII polypeptides, and also renders it possible to suppress the formation of such late eluting peaks.

Thus, in preferred embodiments, the purified drug substance of the Factor VII polypeptide collected in step (c) comprises less than 50% of, e.g., late eluting peaks compared to the drug substance in step (a), e.g. less than 40%, or less than 30%.

In one embodiment, the content of oxidized forms in the purified drug substance of the Factor VII polypeptide collected in step (c) is reduced with at least 35%, such as e.g. at least 40 or 45%, compared to the content of the drug substance in step (a). In another embodiment, the content of proteolytically degraded forms in the purified drug substance of the Factor VII polypeptide collected in step (c) is reduced with at least 30%, such as e.g. at least 32% or 38%, compared to the content in the drug substance in step (a). In another embodiment, the content of Factor VII polypeptides lacking one or more N-linked glycans (des-N-glycan forms) in the purified drug substance of the Factor VII polypeptide collected in step (c) is reduced with at least 40%, such as e.g. at least 50%, 60%, 70% or 75%, compared to the content in the drug substance in step (a).

Typically, the HIC process of the present invention is capable reducing the content of late eluting peaks with at least 50%, however more preferably, and also realistically, the reduction is at least 60%, such as at least 70% or even at least 80% or at least 85%.

More particularly, the purified drug substance of the Factor VII polypeptide comprises at the most 5%, such as at the most 2%, or at the most 1.5%, preferably, at the most 1% or at the most 5%, of late eluting peaks or other product-related impurities.

Usually, the hydrophobic interaction chromatography material is regenerated for the purpose of subsequent use by a sequence of steps.

It should be noted that the washing step and the elution step need not to be discrete steps, but may be combined, in particular if a gradient elution buffer is utilized in the elution step.

The HIC purification process described above is particularly useful for obtaining a purified drug substance of a Factor VII polypeptide, and if the conditions for the steps (a)-(c) with respect to pH are selected properly, it is even possible to reduce the formation of late eluting peaks and thereby increase the overall yield of the process.

In a particular aspect, the invention provides a process for the purification of a drug substance of a Factor VII polypeptide, said drug substance comprising at least 3% of late eluting peaks, said process comprising the steps of: (a) contacting the drug substance with a hydrophobic interaction chromatography material under conditions which facilitate binding of a portion of said drug substance to said hydrophobic interaction chromatography material, said drug substance comprising an ammonium salt in a concentration of in the range of 1.5-2.5 M; (b) washing said hydrophobic interaction chromatography material with a washing buffer comprising the ammonium salt in a concentration of in the range of 1.5-2.5 M, typically substantially the same concentration as in step (a); and (c) eluting said hydrophobic interaction chromatography material with an elution buffer comprising an ammonium salt, said elution buffer being a gradient buffer with respect to the ammonium salt, and collecting a purified drug substance of the Factor VII polypeptide as an eluate, wherein steps (b) and (c) may be combined.

Preferably, the elution buffer in step (c) is a gradient buffer with respect to the an ammonium salt, wherein the initial concentration of the ammonium salt of the gradient buffer is in the range of 1.8-2.2 M, and the final concentration of the ammonium salt of the gradient buffer is in the range of 0.0-0.2 M. The ammonium salt is preferably ammonium acetate or ammonium sulphate (when calcium is absent).

After collection of the fractions corresponding to the purified drug substance of the Factor VII polypeptide, may be formulated into a solution, which may be dispensed into vials and freeze-dried or store as such. As an illustrative example of a final product corresponding to the commercially available, recombinantly-made FVII polypeptide composition NovoSeven® (Novo Nordisk A/S, Denmark), can be mentioned—e.g., a vial (1.2 mg) containing 1.2 mg recombinant human Factor VIIa, 5.84 mg NaCl, 2.94 mg $CaCl_2$, $2H_2O$, 2.64 mg GlyGly, 0.14 mg polysorbate 80, and 60.0 mg mannitol. This product is reconstituted to pH 5.5 by 2.0 mL water for injection (WFI) prior to use. When reconstituted, the protein solution is stable for use for 24 hours.

The overall manufacture of recombinant activated Factor VII (rFVIIa) is described by Jurlander, et al. in Seminars in Thrombosis and Hemostasis, Vol. 27, No. 4, 2001.

As already mentioned, in addition to providing methods for reducing product-related impurities, the present invention also provides methods for producing a Factor VII polypeptide preparation comprising a predetermined serine/threonine-linked glycoform pattern and/or for purifying a O-glycosylated polypeptide having a desired glycoform pattern from a composition comprising said polypeptide and polypeptides having unwanted glycoform patterns by application of HIC purification.

The pattern of oligosaccharides for a Factor VII polypeptide may be determined using any method known in the art, including, without limitation: high-performance liquid chromatography (HPLC); capillary electrophoresis (CE); nuclear magnetic resonance (NMR); mass spectrometry (MS) using ionization techniques such as fast-atom bombardment, electrospray, or matrix-assisted laser desorption (MALDI); gas chromatography (GC); and treatment with exoglycosidases in conjunction with anion-exchange (AIE)-HPLC, size-exclusion chromatography (SEC), or MS. See, e.g., Weber et al., Anal. Biochem. 225:135 (1995); Klausen et al., J. Chromatog. 718:195 (1995); Morris et al., in Mass Spectrometry of Biological Materials, McEwen et al., eds., Marcel Dekker, (1990), pp 137-167; Conboy et al., Biol. Mass Spectrum. 21:397, 1992; Hellerqvist, Meth. Enzymol. 193:554 (1990); Sutton et al., Anal. Biochem. 318:34 (1994); Harvey et al., Organic Mass Spectrometry 29:752 (1994).

The hydrophobic interaction chromatography material used in such methods typically is a matrix substituted with hydrophobic ligands such as ethyl, butyl, phenyl or hexyl (which appears to be responsible for binding the protein). Preferred materials are those substituted with phenyl ligands. The material is most often presented in the form of beads, e.g. a particulate material having an average diameter of in the range of 0.1-1000 μm, or in the form of sticks, membranes, pellets, monoliths, etc.

The most common arrangement of the hydrophobic interaction chromatography material is in a column format. Arrangement in a batch container is of course also possible.

In one particular aspect, invention provides a method comprising the following steps: (a) obtaining a preparation of a Factor VII glycoprotein containing a Cys-X1-Ser/Thr-X2-Pro-Cys motif and wherein said serine/threonine forms part of a Glc-O-Ser/Thr covalent bond from a cell in which it is prepared; e.g., from an engineered cell (cell culture) or by isolating the glycoprotein from a natural source; (b) binding the glycoprotein to an hydrophobic interaction material using a solution comprising water, optionally a salt component, and optionally a buffer; (c) optionally washing the hydrophobic interaction material using a solution comprising water, optionally a salt component, and optionally a buffer so as to elute contaminants from the hydrophobic interaction material; (d) washing the hydrophobic interaction material using a solution comprising an organic modifier, water, optionally a salt component, and optionally a buffer, at a linear or step gradient or isocratically in salt component so as to separate glycoproteins having a desired glycoform pattern from glycoproteins not having the desired glycoform from the hydrophobic interaction material; and (e) collecting the fraction containing the Factor VII glycoprotein(s) having the desired glycoform pattern. In one embodiment, the above-described method further includes the step of repeating steps (a) to e) by subjecting the preparation obtained in step (e) to steps (a) to (e). This further step may be repeated more than once if deemed necessary.

In a preferred embodiment, the above-described method utilizes the isolation of a Factor VII polypeptide exhibiting substantially uniform Xyl-Xyl-Glc-O-Ser52 glycosylation and/or a Factor VII polypeptide exhibiting substantially uniform Glc-O-Ser52 glycosylation.

As used herein, a "glycoform pattern" (or "glycosylation pattern") refers to the distribution within the preparation of oligosaccharide chains having varying structures that are covalently linked to a serine or threonine residue located in the amino acid backbone of the polypeptide.

"Homogeneity" refers to the structural consistency across a population of polypeptides with conjugated glycans. Thus, a glycoprotein preparation is said to be about 100% homologous if all contained glycoprotein molecules contain identical glycans attached to the relevant glycosylation site. For example, a preparation of Factor VII polypeptides is said to be at least 90% homologous if at least 90% of the Factor VII polypeptide molecules contain the glycan of interest attached to serine 52 (e.g., Xyl-Xyl-Glc-O-Ser52). Such preparations are obtainable by practice of the HIC purification methods provided herein.

"Substantially uniform glycoform" or "substantially uniform glycosylation" or "substantially uniform glycosylation pattern", when referring to a glycopeptide species, refers to the percentage of acceptor moieties, i.e., serine or threonine residues, that are glycosylated by the glycan of interest. For example, in the case of Factor VII, a substantially uniform glycosylation patterns exists if substantially all (as defined below) of the serine residues in position 52 are glycosylated with the glycan of interest. It is understood by one skilled in the art that the starting material may contain glycosylated serine and/or threonine residues that are glycosylated with a species having the same structure as the glycan of interest. Thus, the calculated percent glycosylation includes serine/threonine residues that are glycosylated with the glycan of interest according to the invention, as well as those serine/threonine residues already glycosylated with the glycan of interest in the starting material.

The term "substantially" in connection with the preparation of Factor VII polypeptides with relatively glycoform patterns means that at least about 80%, such as at least about 90%, at least about 95%, or at least about 98% of the serine/threonine residues in the glycoprotein product is glycosylated with a predetermined, specific glycan or glycan of interest. The glycosylation pattern is typically determined by one or more methods known to those skilled in the art, such as, e.g., tryptic digestion followed by high performance liquid chromatography (HPLC), liquid-chromatography-mass spectrometry (LC-MS), matrix assisted laser desorption mass time of flight spectrometry (MALDITOF), capillary electrophoresis, and the like.

In another embodiment the isolated glycoproteins prepared by the above-described method are: Factor VII-related polypeptides exhibiting substantially uniform Xyl-Xyl-Glc-O-Ser52 glycosylation; Factor VII-related polypeptides exhibiting substantially uniform Glc-O-Ser52 glycosylation; Factor VII variants exhibiting substantially uniform Xyl-Xyl-Glc-O-Ser52 glycosylation; and Factor VII variants exhibiting substantially uniform Glc-O-Ser52 glycosylation.

The above-described methods may further comprise the step of subjecting preparations having predetermined glycoform patterns to at least one test of bioactivity (including, e.g., clotting, Factor X proteolysis, or TF binding) or other functionality (such as, e.g., pharmacokinetic profile or stability), and correlating particular glycoform patterns with particular bioactivity or functionality profiles in order to identify a desired glycoform pattern.

Further enzymatic treatments may be used in connection with the above methods to modify the oligosaccharide pattern of N- or O-linked glycans of a preparation; such treatments include, without limitation, treatment with one or more of sialidase (neuraminidase), galactosidase, fucosidase; galactosyl transferase, fucosyl transferase, and/or sialyltransferase, in a sequence and under conditions that achieve a desired modification in the distribution of oligosaccharide chains having particular terminal structures. Glycosyl transferases are commercially available from Calbiochem (La Jolla, Calif.) and glycosidases are commercially available from Glyko, Inc., (Novato, Calif.).

Preparations of glycoproteins having predetermined oligosaccharide patterns according to the invention (including Factor VII polypeptides and Factor VII-related polypeptides) exhibit improved functional properties relative to reference preparations. The improved functional properties may include, without limitation, a) physical properties such as, e.g., storage stability; b) pharmacokinetic properties such as, e.g., bioavailability and half-life; c) immunogenicity in humans, and d) biological activity, such as, e.g., clotting activity.

Storage stability of a glycoprotein (e.g., Factor VII) preparation may be assessed by measuring (a) the time required for 20% of the bioactivity of a preparation to decay when stored as a dry powder at 25° C. and/or (b) the time required for a doubling in the proportion of (e.g., Factor VIIa) aggregates of said glycoprotein in the preparation.

In some embodiments, preparations of the invention exhibit an increase of at least about 30%, preferably at least about 60% and more preferably at least about 100%, in the time required for 20% of the bioactivity to decay relative to the time required for the same phenomenon in a reference preparation, when both preparations are stored as dry powders at 25° C. Bioactivity measurements may be performed using any of a clotting assay, proteolysis assay, TF-binding assay, or TF-independent thrombin generation assay.

In some embodiments, the preparations of the invention exhibit an increase of at least about 30%, preferably at least about 60%, and more preferably at least about 100%, in the time required for doubling of aggregates relative to a reference preparation, when both preparations are stored as dry powders at 25° C. The contents of aggregates may be determined according to methods known to the skilled person, such as, e.g., gel permeation HPLC methods. For example, the content of Factor VII aggregates is determined by gel permeation HPLC on a Protein Pak 300 SW column (7.5×300 mm) (Waters, 80013) as follows. The column is equilibrated with Eluent A (0.2 M ammonium sulfate, 5% isopropanol, pH adjusted to 2.5 with phosphoric acid, and thereafter pH is adjusted to 7.0 with triethylamine), after which 25 µg of sample is applied to the column. Elution is with Eluent A at a flow rate of 0.5 ml/min for 30 min, and detection is achieved by measuring absorbance at 215 nm. The content of aggregates is calculated as the peak area of the Factor VII aggregates/total area of Factor VII peaks (monomer and aggregates).

"Bioavailability" refers to the proportion of an administered dose of a (e.g., Factor VII or Factor VII-related) glycoprotein preparation that can be detected in plasma at predetermined times after administration. Typically, bioavailability is measured in test animals by administering a dose of between about 25-250 µg/kg of the preparation; obtaining plasma samples at predetermined times after administration; and determining the content of (e.g., Factor VII or Factor VII-related) glycosylated polypeptides in the samples using one or more of a clotting assay (or any bioassay), an immunoassay, or an equivalent. The data are typically displayed graphically as polypeptide [e.g., Factor VII] v. time and the bioavailability is expressed as the area under the curve (AUC). Relative bioavailability of a test preparation refers to the ratio between the AUC of the test preparation and that of the reference preparation.

In some embodiments, the preparations of the present invention exhibit a relative bioavailability of at least about 110%, preferably at least about 120%, more preferably at least about 130% and most preferably at least about 140% of the bioavailability of a reference preparation. The bioavailability may be measured in any mammalian species, preferably dogs, and the predetermined times used for calculating AUC may encompass different increments from 10 min-8 h.

"Half-life" refers to the time required for the plasma concentration of (e.g., Factor VII polypeptides of Factor VII-related polypeptides) the glycoprotein to decrease from a particular value to half of that value. Half-life may be determined using the same procedure as for bioavailability. In some embodiments, the preparations of the present invention exhibit an increase in half-life of at least about 0.25 h, preferably at least about 0.5 h, more preferably at least about 1 h, and most preferably at least about 2 h, relative to the half-life of a reference preparation.

"Immunogenicity" of a preparation refers to the ability of the preparation, when administered to a human, to elicit a deleterious immune response, whether humoral, cellular, or both. Factor VIIa polypeptides and Factor VIIa-related polypeptides are not known to elicit detectable immune responses in humans. Nonetheless, in any human sub-population, there may exist individuals who exhibit sensitivity to particular administered proteins. Immunogenicity may be measured by quantifying the presence of anti-Factor VII antibodies and/or Factor VII-responsive T-cells in a sensitive individual, using conventional methods known in the art. In some embodiments, the preparations of the present invention exhibit a decrease in immunogenicity in a sensitive individual of at least about 10%, preferably at least about 25%, more preferably at least about 40% and most preferably at least about 50%, relative to the immunogenicity for that individual of a reference preparation.

Preparations of the present invention may be used to treat any syndrome responsive to the relevant Factor VII polypeptide. Factor VII-responsive syndromes, respectively, include syndromes such as, e.g., bleeding disorders, including, without limitation, those caused by clotting factor deficiencies; by thrombocytopenia; or by clotting factor inhibitors, or excessive bleeding from any cause. Preparations may also be administered to patients in association with surgery or other trauma or to patients receiving anticoagulant therapy.

Preparations comprising Factor VII-related polypeptides according to the invention, which have substantially reduced bioactivity relative to wild-type Factor VII, may be used as anticoagulants, such as, e.g., in patients undergoing angioplasty or other surgical procedures that may increase the risk of thrombosis or occlusion of blood vessels as occurs, e.g., in restenosis. Other medical indications for which anticoagulants are prescribed include, without limitation, deep vein thrombosis, pulmonary embolism, stroke, disseminated intravascular coagulation (DIC), fibrin deposition in lungs and kidneys associated with gram-negative endotoxemia, myocardial infarction; Acute Respiratory Distress Syndrome (ARDS), Systemic Inflammatory Response Syndrome (SIRS), Hemolytic Uremic Syndrome (HUS), MOF, and TTP.

Pharmaceutical compositions comprising the Factor VII and Factor VII-related preparations according to the present are primarily intended for parenteral administration for prophylactic and/or therapeutic treatment. Preferably, the pharmaceutical compositions are administered parenterally, i.e., intravenously, subcutaneously, or intramuscularly. They may be administered by continuous or pulsatile infusion.

Pharmaceutical compositions or formulations comprise a preparation according to the invention in combination with, preferably dissolved in, a pharmaceutically acceptable carrier, preferably an aqueous carrier or diluent. A variety of aqueous carriers may be used, such as water, buffered water, 0.4% saline, 0.3% glycine and the like. The preparations of the invention can also be formulated into liposome preparations for delivery or targeting to the sites of injury. Liposome preparations are generally described in, e.g., U.S. Pat. Nos. 4,837,028, 4,501,728, and 4,975,282. The compositions may be sterilized by conventional, well-known sterilization techniques. The resulting aqueous solutions may be packaged for use or filtered under aseptic conditions and lyophilized, the preparation being combined with a sterile aqueous solution prior to administration.

Compositions of the invention may contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc.

The concentration of Factor VII or Factor VII-related polypeptides in these formulations can vary widely, i.e., from less than about 0.5% by weight, usually at or at least about 1% by weight to as much as 15 or 20% by weight and will be selected primarily by fluid volumes, viscosities, etc., in accordance with the particular mode of administration selected.

Thus, a typical pharmaceutical composition for intravenous infusion could be made up to contain 250 ml of sterile Ringer's solution and 10 mg of the preparation. Actual methods for preparing parenterally administrable compositions will be known or apparent to those skilled in the art and are described in more detail in, for example, Remington's Pharmaceutical Sciences, 18th ed., Mack Publishing Company, Easton, Pa. (1990).

The compositions containing the preparations of the present invention can be administered for prophylactic and/or therapeutic treatments. In therapeutic applications, compositions are administered to a subject already suffering from a disease, as described above, in an amount sufficient to cure, alleviate or partially arrest the disease and its complications. An amount adequate to accomplish this is defined as "therapeutically effective amount". Effective amounts for each purpose will depend on the severity of the disease or injury as well as the weight and general state of the subject. In general, however, the effective amount will range from about 0.05 mg up to about 500 mg of the preparation per day for a 70 kg subject, with dosages of from about 1.0 mg to about 200 mg of the preparation per day being more commonly used. It will be understood that determining an appropriate dosage may be achieved using routine experimentation, by constructing a matrix of values and testing different points in the matrix.

Local delivery of the preparations of the present invention, such as, for example, topical application, may be carried out, e.g., by means of a spray, perfusion, double balloon catheters, stents, incorporated into vascular grafts or stents, hydrogels used to coat balloon catheters, or other well established methods. In any event, the pharmaceutical compositions should provide a quantity of the preparation sufficient to effectively treat the subject.

The pharmaceutical compositions of the invention may further comprise other bioactive agents, such as, e.g., non-Factor VII-related coagulants or anticoagulants.

EXPERIMENTALS

General Methods

Assays Suitable for Determining Biological Activity of Factor VII Polypeptides

Factor VII polypeptides useful in accordance with inventive methods described herein may be selected by suitable assays that can be performed as simple preliminary in vitro tests. Thus, the present specification discloses a simple test (entitled "In Vitro Hydrolysis Assay") for the activity of Factor VII polypeptides.

1st Generation Clot Assay

The activity of Factor VII polypeptides may be measured using a one-stage clot assay essentially as described in WO 92/15686 or U.S. Pat. No. 5,997,864. Briefly, the sample to be tested is diluted in 50 mM Tris (pH 7.5), 0.1% BSA and 100 µL is incubated with 100 µL of Factor VII deficient plasma and 200 µL of thromboplastin C containing 10 mM Ca2+. Clotting times are measured and compared to a standard curve using a reference standard or a pool of citrated normal human plasma in serial dilution.

In Vitro Hydrolysis Assay (Assay 1)

Native (wild-type) Factor VIIa and Factor VII polypeptide (both hereinafter referred to as "Factor VIIa") may be assayed for specific activities. They may also be assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM HEPES, pH 7.4, containing 0.1 M NaCl, 5 mM $CaCl_2$ and 1 mg/mL bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used for calculating the ratio between the activities of Factor VII polypeptide and wild-type Factor VIIa:

Ratio=($A405$ nm Factor VII polypeptide)/($A405$ nm Factor VIIa wild-type).

Based thereon, Factor VII polypeptides with an activity lower than, comparable to, or higher than native Factor VIIa may be identified, such as, for example, Factor VII polypeptides where the ratio between the activity of the Factor VII polypeptide and the activity of native Factor VII (wild-type FVII) is about 1.0 versus above 1.0.

The activity of the Factor VII polypeptides may also be measured using a physiological substrate such as Factor X ("In Vitro Proteolysis Assay"), suitably at a concentration of 100-1000 nM, where the Factor Xa generated is measured after the addition of a suitable chromogenic substrate (e.g., S-2765). In addition, the activity assay may be run at physiological temperature.

In Vitro Proteolysis Assay (Assay 2)

Native (wild-type) Factor VIIa and Factor VII polypeptide (both hereinafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 µL 50 mM HEPES, pH 7.4, containing 0.1 M NaCl, 5 mM $CaCl_2$ and 1 mg/mL bovine serum albumin, are incubated for 15 min. Factor X cleavage is then stopped by the addition of 50 µL 50 mM HEPES, pH 7.4, containing 0.1 M NaCl, 20 mM EDTA and 1 mg/mL bovine serum albumin. The amount of Factor Xa generated is measured by the addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used for calculating the ratio between the proteolytic activities of Factor VII polypeptide and wild-type Factor VIIa:

Ratio=($A405$ nm Factor VII polypeptide)/($A405$ nm Factor VIIa wild-type).

Based thereon, a Factor VII polypeptide with an activity lower than, comparable to, or higher than native Factor VIIa may be identified, such as, for example, Factor VII polypeptides where the ratio between the activity of the Factor VII polypeptide and the activity of native Factor VII (wild-type FVII) is about 1.0 versus above 1.0.

Thrombin Generation Assay (Assay 3)

The ability of a Factor VII polypeptides to generate thrombin can be measured in an assay (Assay 3) comprising all relevant coagulation Factors and inhibitors at physiological concentrations (minus Factor VIII when mimicking hemophilia A conditions) and activated platelets (as described on p. 543 in Monroe et al. (1997) Brit. J. Haematol. 99, 542-547 which is hereby incorporated as reference).

One-stage Coagulation Assay (Clot Assay) (Assay 4)

Factor VII polypeptides may also be assayed for specific activities ("clot activity") by using a one-stage coagulation assay (Assay 4). For this purpose, the sample to be tested is diluted in 50 mM PIPES-buffer (pH 7.2), 1% BSA and 40 µl is incubated with 40 µl of Factor VII deficient plasma and 80 µl of human recombinant tissue factor containing 10 mM $Ca^{2+}$ and synthetic phospholipids. Coagulation times (clotting times) are measured and compared to a standard curve using a reference standard in a parallel line assay.

RP-HPLC Assay Suitable for Determination of "Relative Retention Time" and Content of Oxidized FVII, Heavy Chain Degraded FVII and "Late Eluting Peaks"

"Late eluted peaks" are those eluting with a higher retention relative to that of the Factor VII polypeptide of interest in a RP-HPLC assay, e.g. as described in the following:

Reverse phase HPLC was run on an in-house produced butyl-bonded silica column (4.5×250 mm) with a particle size of 5 µm and pore size 300 Å; (comparable results can be obtained with an ACE C4, 5 µm, 300 Å, 4.6×250 mm column).

Column temperature: 70° C. A-buffer: 0.1% v/v trifluoracetic acid. B-buffer: 0.09% v/v trifluoracetic acid, 80% v/v acetonitrile.

The column was eluted with a linear gradient from X to (X+13) % B in 30 minutes. X was adjusted so that FVIIa elutes with a retention time of approximately 26 minutes.

Flow rate: 1.0 mL/min. Detection: 214 nm. Load: 25 µg FVIIa.

Figure 15:
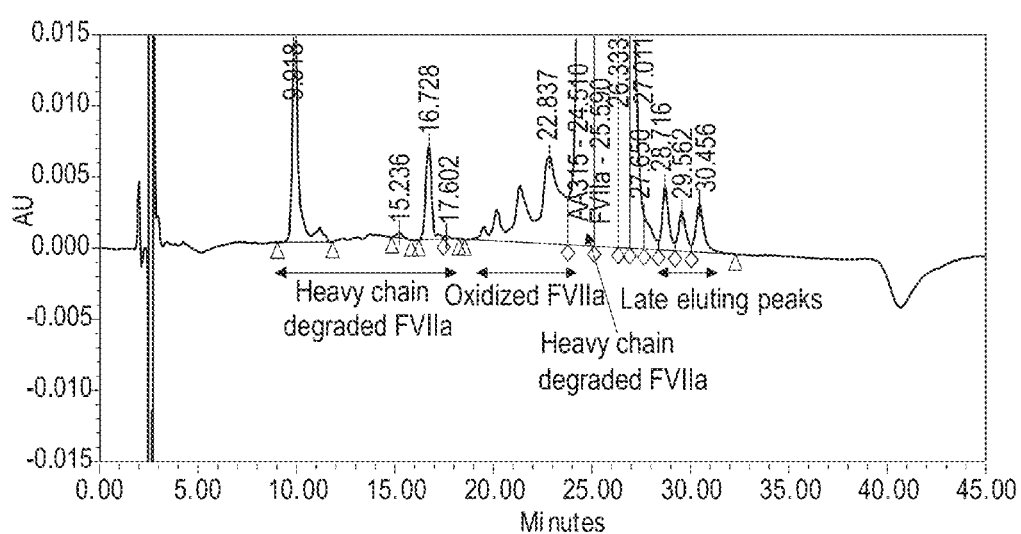
FIG. 15 illustrates a HPLC chromatogram of FVII and its product-related impurities.

FIG. 15 shows a HPLC chromatogram of FVII and its product-related impurities.

Content of Aggregates

The content of aggregates is determined by non-denaturing size exclusion HPLC (SEHPLC). Non-denaturing size exclusion chromatography was run on a Waters Protein Pak 300

SW column, 7.5×300 mm using 0.2 M ammonium sulphate, 5% 2-propanol pH 7.0 as mobile phase. Flow rate: 0.5 mL/min. Detection: 215 nm. Load: 25 µg FVIIa.

Determination of Content of desGla-Factor VII Polypeptide Structures

The content of desGla-Factor VII polypeptide structures relative to the full length Factor VII polypeptide structures is determined by SDS-PAGE. 150 µl of sample is added 50 µl of sample buffer (non-reducing, NuPAGE) and boiled for 5 mins. A 10 µl sample is loaded onto a 12% BisTris NuPAGE Gel (Invitrogen). The gel is run at 200 Volts, 120 mA for 55 mins. The gel is stained using coomassie brilliant blue solution, destained and dried. The relative desGla-Factor VII polypeptide content is calculated as the area of the desGla-Factor VII polypeptide band divided by the areas of the Factor VII polypeptide band at approx. 50 kDa and desGla-Factor VII polypeptide band at approx. 45 kDa.

Alternatively, the content of desGla-Factor VII polypeptide structures may be determined by anion exchange HPLC. The method separates Gla-domain-less Factor VII polypeptides from intact Factor VII polypeptides. The content of Gla-domain-less Factor VII polypeptides is expressed in % of the Factor VII polypeptide related peak area. As analytical column is used a DNAPac PA-100, 250×4 mm (Dionex Corp.). The column is eluted with a linear gradient from 0-0.5 M ammonium acetate at pH 9.0 over 30 minutes at a flow of 1.0 mL/min. The absorbance at 280 nm of the effluent is monitored.

Determination of Content of Factor VII Polypeptide Structures Lacking One or More N-Linked Glycans The content of Factor VII polypeptide structures lacking one or both N-linked glycans may be determined using, e.g., high-performance liquid chromatography (HPLC); capillary electrophoresis (CE); or mass spectrometry (MALDI-MS and LC-MS).

For example, when using MALDI-MS, peaks appearing with mass of about 50 kDa, 47.5 kDa and 45 kDa designate Factor VII polypeptides having both N-linked glycans and Factor VII lacking one or both glycans, respectively.

The pattern of N-linked oligosaccharides may be determined using any method known in the art, including, without limitation: high-performance liquid chromatography (HPLC); capillary electrophoresis (CE); nuclear magnetic resonance (NMR); mass spectrometry (MS) using ionization techniques such as fast-atom bombardment, electrospray, or matrix-assisted laser desorption (MALDI); gas chromatography (GC); and treatment with exoglycosidases in conjunction with anion-exchange (AIE)-HPLC, size-exclusion chromatography (SEC), or MS. See, e.g., Weber et al., *Anal. Biochem.* 225:135 (1995); Klausen et al., *J. Chromatog.* 718:195 (1995); Morris et al., in *Mass Spectrometry of Biological Materials*, McEwen et al., eds., Marcel Dekker, (1990), pp 137-167; Conboy et al., *Biol. Mass Spectrom.* 21:397, 1992; Hellerqvist, *Meth. Enzymol.* 193:554 (1990); Sutton et al., *Anal. Biochem.* 318:34 (1994); Harvey et al., *Organic Mass Spectrometry* 29:752 (1994).

Following resolution of Factor VII glycoforms using any of the above methods, the resolved species are assigned to different groups (i)-(iii). The relative content of each of (i)-(iii) is calculated as the sum of the glycoforms assigned to that group relative to the total content of glycoforms in the sample.

Figure 14:
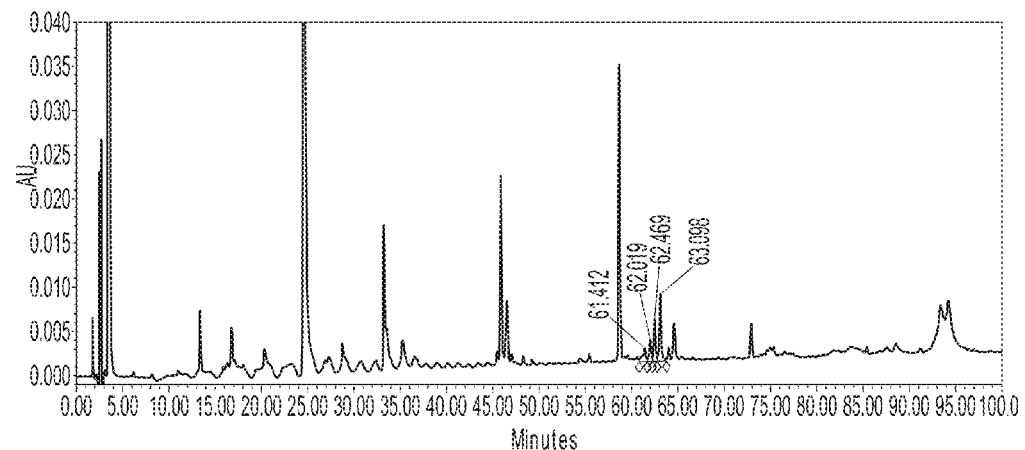
FIG. 14 is an RP-HPLC chromatogram of tryptic digest of the rFVIIa light chain.

Analysis of O-Glycoform Pattern of rFVIIa (a) Tryptic Peptide Mapping of the rFVIIa Light Chain The relative content of the O-glycoforms of rFVIIa is determined by tryptic peptide mapping of the rFVIIa light chain. The rFVIIa is reduced and alkylated and the rFVIIa light chain is purified on a RP-HPLC column eluted with an acetonitrile gradient in water:trifluoroacetic acid. The purified rFVIIa light chain is buffer-exchanged to Tris buffer, pH 7.5 and digested with trypsin. The tryptic digest of the rFVIIa light chain is analyzed on a RP-HPLC column (for example Nucleosil C18, 5 µm, 300 Å, 4.0×250 mm, Macherey-Nagel 720065) eluted with an acetonitrile gradient (0%-45% acetonitrile in 100 min) in water: trifluoroacetic acid (see FIG. 14). Flow is 1.0 ml/min and detection is UV at 215 nm.

The peaks containing the O-glycopeptides of rFVIIa are eluted after approx. 60-65 min where the 1st and the 3rd peak contain O-glycopeptides with a xylose-xylose-glucose-linked to serine 52, and the 2nd and 4th peak contain O-glycopeptides with a glucose linked to serine 52.

Similarly, the 1st and the 2nd peak contain O-glycopeptides with a tetrasaccharide linked to serine 60, and the 3rd and the 4th peak contain O-glycopeptides with a fucose linked to serine 60.

(b) Tryptic Peptide Mapping of rFVIIa

The O-glycoform pattern can be analyzed by tryptic peptide mapping of rFVIIa. The rFVIIa is buffer-exchanged to Tris buffer, pH 7.5, and digested with trypsin. The tryptic digest of the rFVIIa is analyzed on a RP-HPLC column (for example Nucleosil C18, 5 µm, 300 Å, 4.0×250 mm, Macherey-Nagel 720065) eluted with an acetonitrile gradient (0%-45% acetonitrile in 100 min) in water: trifluoroacetic acid. Flow is 1.0 ml/min and detection is UV at 215 nm.

The peaks containing the O-glycopeptides of rFVIIa are eluted after approx. 67-70 min where the 1st peak contains O-glycopeptides with a xylose-xylose-glucose linked to serine 52, and the 2nd peak contains O-glycopeptides with a glucose linked to serine 52.

(c) Total Mass Analysis of rFVIIa

The O-glycoform pattern can be analyzed by total mass analysis of rFVIIa. The rFVIIa is desalted on a Millipore ZipTip C4 column equilibrated with 1% formic acid and eluted with 3% formic acid in 90% methanol. The eluted sample is analyzed by the nanospray technique on a Qstar XL mass spectrometer.

The major peak at approximately 50,500 Da represents rFVIIa O-glycoforms with a glucose linked to serine 52 and the major peak at approximately 50,800 Da represents rFVIIa O-glycoforms with a xylose-xylose-glucose linked to serine 52.

EXAMPLES

The following examples illustrate the invention. These examples are included for illustrative purposes only and are not intended in any way to limit the scope of the invention claimed.

Example 1

Reduction of Heavy Chain Degraded and Oxidized rhFVII by HIC Purification of rhFVIIa at DH 6 Using TSK Phenyl 5PW 5 mg of highly pure recombinant hFVIIa was added NH$_4$-acetate to a final concentration of 1.8 M and CaCl$_2$ to a final concentration of 10 mM and methionine to a final concentration of 10 mM. pH was adjusted to pH 6.0. This sample was added to a column (0.5 cm in inner diameter×10.0 cm length=2 ml column volume (CV)) packed with Toso Haas TSK-Gel phenyl 5 PW, equilibrated with 5 CV 1.8 M NH$_4$-acetate, 10 mM CaCl$_2$, 10 mM methionine, pH 6.0 (load 1.6 g/L). The column was washed with 3 CV 1.8 M NH$_4$-acetate, 10 mM CaCl$_2$, 10 mM methionine, pH 6.0. Elution was performed using an 18 CV linear gradient from 1.8 M NH$_4$-acetate to 50 mM NH$_4$-acetate in a buffer containing 10 mM CaCl$_2$, 10 mM methionine at pH 6.0. Though peak collection at approximately 65% of maximum absorbance (at 280 nm) on the leading edge and at approximately 20% of maximum absorbance on the trailing edge a pool was collected, chromatogram in FIG. 1.

The purification was performed at a flow rate between 6 and 12 CV/h and at a temperature of 5° C. The column was regenerated with 50 mM citrate, pH 7.0 and 0.5 M NaOH.

Analysis of the pool and the applied sample by analytical RP-HPLC showed reduction of heavy chain degraded and oxidized rhFVII as shown in Table 1.

TABLE 1

| Sample | Heavy chain degradation | Oxidized FVII |
|---|---|---|
| Application | 9.9% | 2.9% |
| Pool | 5.9% | 1.5% |

Heavy chain degraded and oxidized rhFVII were primarily reduced because of their relatively lower retention time than unmodified rhFVII and were thus reduced by cutting on the leading edge.

Example 2

Performing Hydrophobic Interaction Chromatography

A sample of rhFVII is added (NH$_4$)$_2$SO$_4$ to a final concentration 1 M. pH is adjusted to pH 8.6 buffered with 20 mM Tris. This sample is added to a column packed with Toyopearl butyl 650S, equilibrated with 5 CV 1 M (NH$_4$)$_2$SO$_4$, 20 mM Tris, pH 8.6. The column is washed with 5 CV 1 M (NH$_4$)$_2$SO$_4$, 20 mM Tris, pH 8.6. Elution is performed using a 20 CV linear gradient from 1.0 M (NH$_4$)$_2$SO$_4$ to 0 M (NH$_4$)$_2$SO$_4$, in a buffer containing 20 mM Tris, pH 8.6. A FVII containing pool is selected through peak collecting. Heavy chain degraded and oxidized rhFVII is reduced due to their lower retention time compared to native rhFVII. The late eluting peaks 1, 2 and 3 are reduced due to their relatively higher retention time compared to the native rhFVII.

Example 3

Reduction of Late Eluting Peaks by HIC Purification of FVIIa Analogue at pH 6 Using TSK Phenyl 5PW A 4.7 ml column was packed with TSK Phenyl 5PW (20 μm) resin and equilibrated with 20 CV of a buffer containing: 2.0 M Ammonium acetate, 10 mM CaCl$_2$, 10 mM Histidine, pH 6.0.

Figure 3:
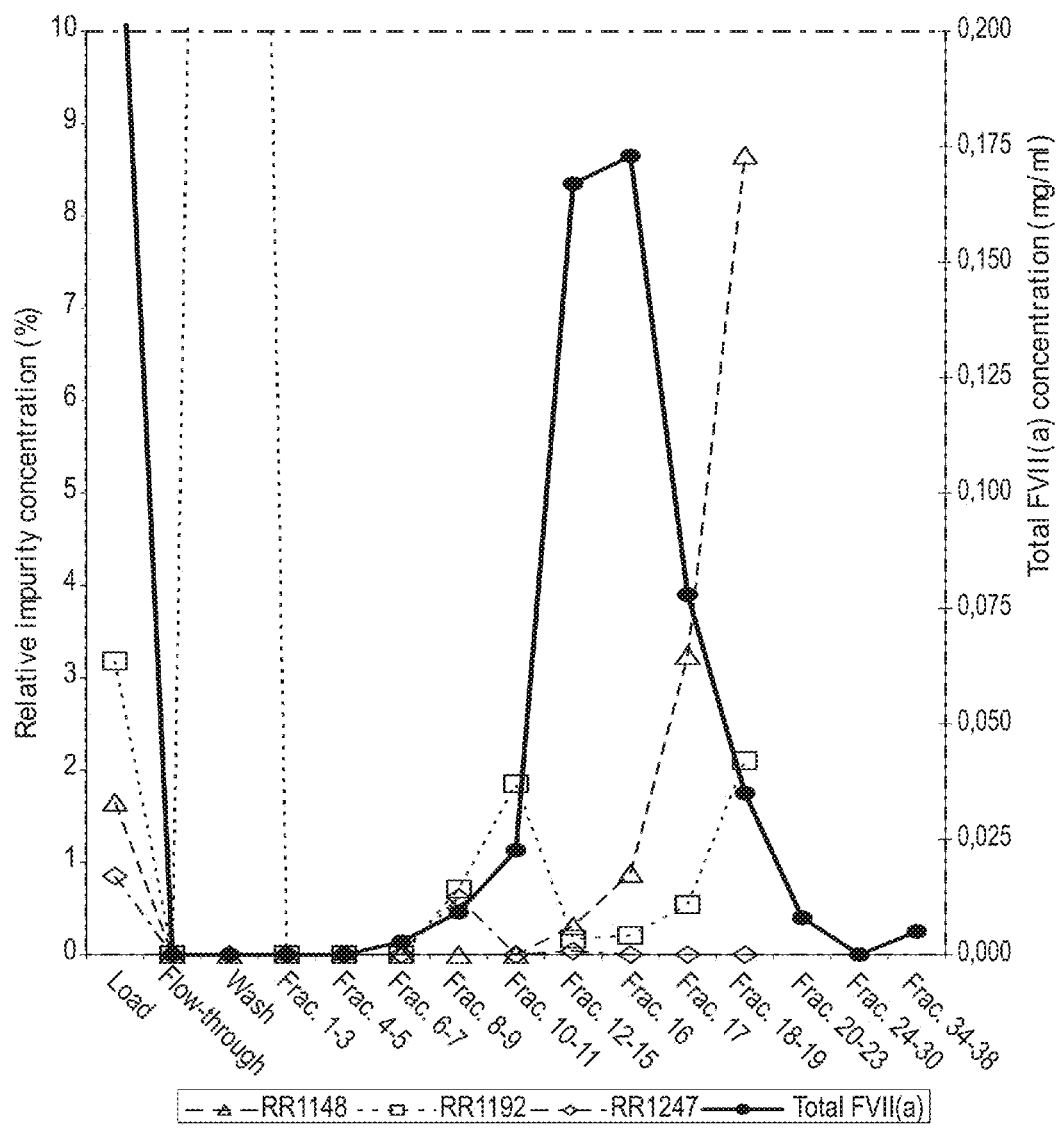
FIG. 3 illustrates elution of impurities throughout the product peak, cf. Example 3.

A load consisting of 15 milliliters of 0.25 mg/ml FVIIa analogue in 2.0 M ammonium acetate, 10 mM CaCl$_2$, 10 mM Histidine, pH 6.0 was loaded onto the column, corresponding to a specific load of 0.8 mg/ml resin. The column was washed using 5 CV of the equilibration buffer. The elution was performed using a linear gradient from the wash and equilibration buffer to 10 mM CaCl$_2$, 10 mM Histidine, pH 6.0 over 10 CV followed by a 5 CV hold. 5 ml fractions were collected across the elution peak. The chromatogram is illustrated in FIG. 3.

The column was regenerated using 5 CV's of 50 mM tri sodium citrate, pH 7.5 followed by 5 CV's of 1.0 M sodium hydroxide. The flow rate was 6 CV/h throughout the purification and a constant temperature of 5° C. was maintained.

Figure 2:
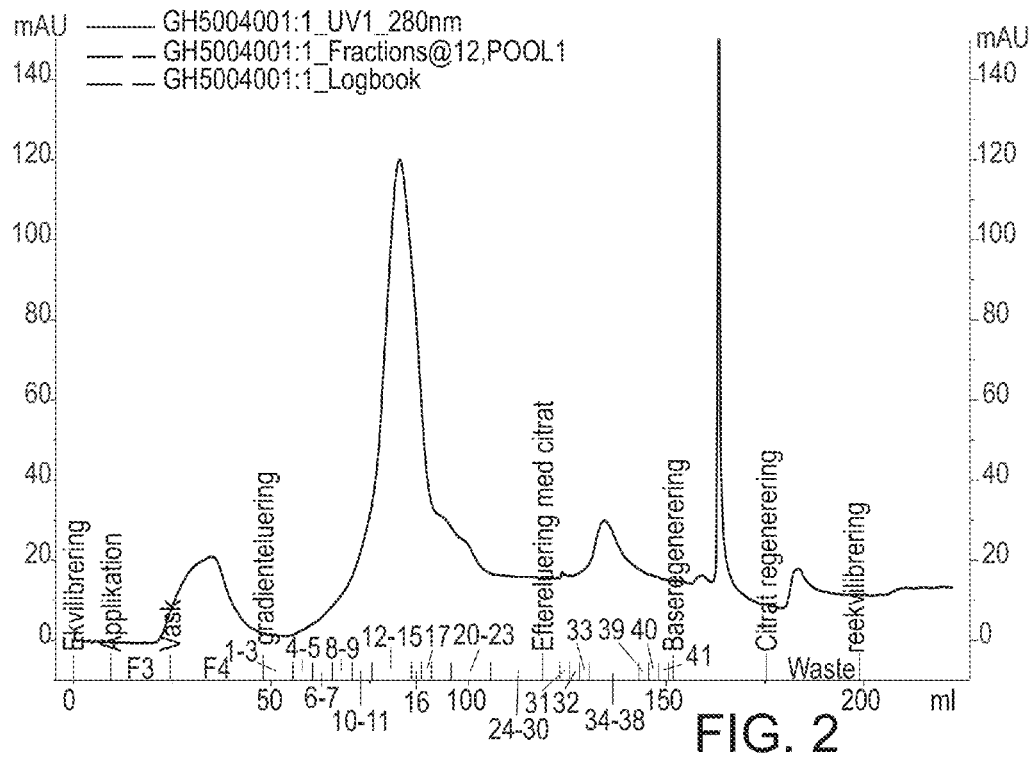
FIG. 2 is a chromatogram of FVIIa analogue separation on TSK Phenyl 5PW, cf. Example 3.

A separation of late eluting peaks with a relative retention (RR)>1000 was achieved as illustrated in the FIG. 2. In total, late eluting peaks (RR1045, RR1066, RR1119, RR1148, RR1192 and RR1247) were reduced by a factor 2.5. The retention of the peaks refers to the relative retention of the respective peak relative to the main product peak in the analytical RP-HPLC system. The collection of fractions 12-17 resulted in a 62% yield.

Example 4

The Reduction of High-Molecular Weight Compounds

Figure 4:
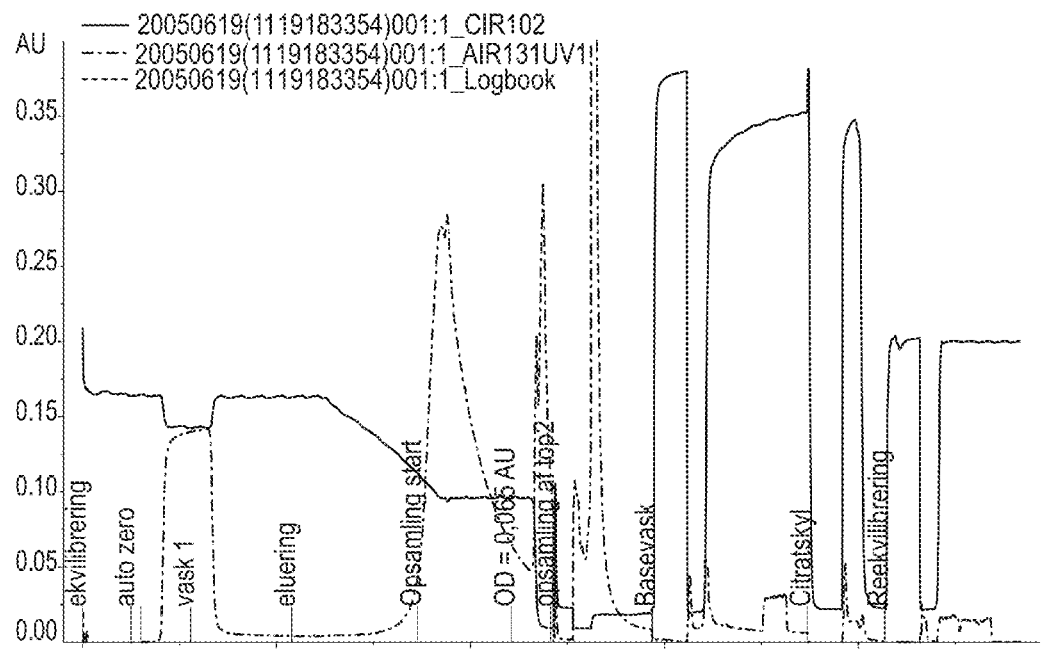
FIG. 4 is a chromatogram of FVIIa analogue separation on TSK Phenyl 5PW, cf. Example 4.

A 2.0 L column was packed with TSK Phenyl 5PW (20 μm) resin and equilibrated with 20 CV of 2.0 M Ammonium acetate, 10 mM CaCl$_2$, 10 mM Histidine, pH 6.0. 5.3 L of a solution containing 0.751 mg/ml FVIIa analogue in 2.0 M ammonium acetate, 10 mM CaCl$_2$, 10 mM Histidine, pH 6.0 was loaded corresponding to a specific load of 2.0 mg/ml resin. The column was washed using 10 CV of the equilibration buffer. The elution was performed using a linear gradient from the wash and equilibration buffer to 10 mM CaCl$_2$, 10 mM Histidine, pH 6.0 over 10 CV followed by a 6.5 CV hold. A pool fraction was collected from 100 mAu (5 mm light path) on the leading edge to 65 mAu (5 mm light path) on the trailing edge. The chromatogram is illustrated in FIG. 4. The pool volume was 9.0 L The column was regenerated using 5 CV's of 50 mM tri sodium citrate, pH 7.5 followed by 5 CV's of 1.0 M sodium hydroxide. The flow rate was 6 CV/h throughout the purification and a constant temperature of 5° C. was maintained.

Figure 5:
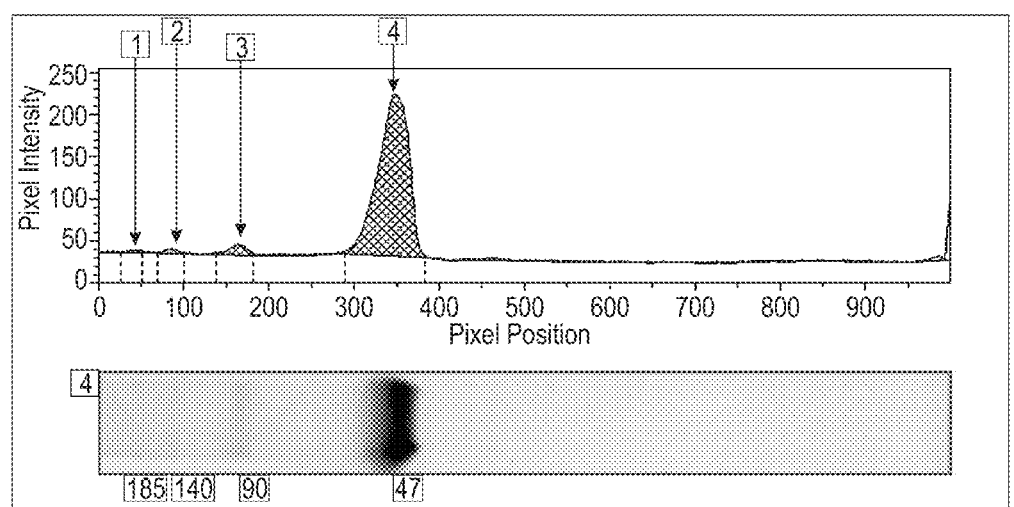
FIG. 5 illustrates an SDS-PAGE of HIC load showing high-molecular weight compounds at 185, 140 and 90 kDa.
Figure 6:
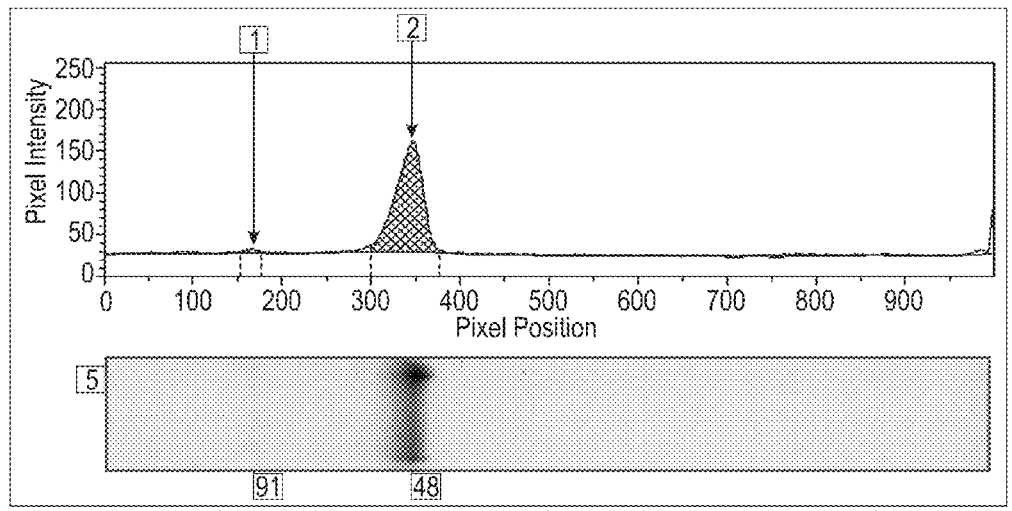
FIG. 6 illustrates an SDS-PAGE of HIC pool showing that the high-molecular weight compounds at 185, 140 and 90 kDa have almost been eliminated.

According to SDS-PAGE, the load contained several components with a molecular weight greater than the product (late eluting peaks). The described purification step reduced all of these to less than half the concentration (see Table 2 and FIGS. 5 and 6).

TABLE 2

|  | Mw (kDa) | Load (%) | Pool (%) | Reduction (fold) |
|---|---|---|---|---|
| FVIIa analogue | 185 | 0.50 | <0.50 | >1.0 |
|  | 148 | 1.11 | <0.50 | >2.2 |
|  | 91 | 3.72 | 1.53 | 2.4 |
|  | 48 | 94.67 | 98.47 |  |

Reduction of Late Eluting Peaks

A sample of the load and pool was analyzed by RP-HPLC as described in REF Y. A reduction of both oxidized forms and late eluting peaks (LE peaks) were seen (see Table 3).

TABLE 3

|  | HIC Load (%) | HIC pool (%) | Reduction fold |
|---|---|---|---|
| Sum of LE peaks | 7.7 | 1.5 | 5.1 |

Example 5

Purification of Glc-O-Ser52-FVII and Xyl-Xyl-Glc-O-Ser52-FVII

Glc-O-ser52-FVII and Xyl-Xyl-Glc-Q-Ser52-FVII was purified using two cycles of hydrophobic interaction chromatography (HIC). The column (1.0 cm in inner diameter×7.0 cm length=5.5 ml column volume (CV)) packed with Toso Haas TSK-Gel phenyl 5 PW, was equilibrated with 5 CV 10 mM histidine, 10 mM $CaCl_2$, 2.0 M $NH_4$-acetate, pH 6.0. The column was loaded with approximately 2.5 mg of FVII pr. ml resin. To the load solution 2.0 M $NH_4$-acetate and 10 mM $CaCl_2$ was added prior to load. The column was washed with 5 CV 10 mM histidine, 10 mM $CaCl_2$, 2.0 M NH4-acetate, pH 6.0. Elution was performed using a 20 CV linear gradient from 10 mM histidine, 10 mM $CaCl_2$, 2.0 M $NH_4$-acetate, pH 6.0 to 10 mM histidine, 10 mM $CaCl_2$, pH 6.0. The purification was performed at a flow rate of 6 CV/h and at a temperature of 5° C. Fractions were collected during elution.

Figure 7:
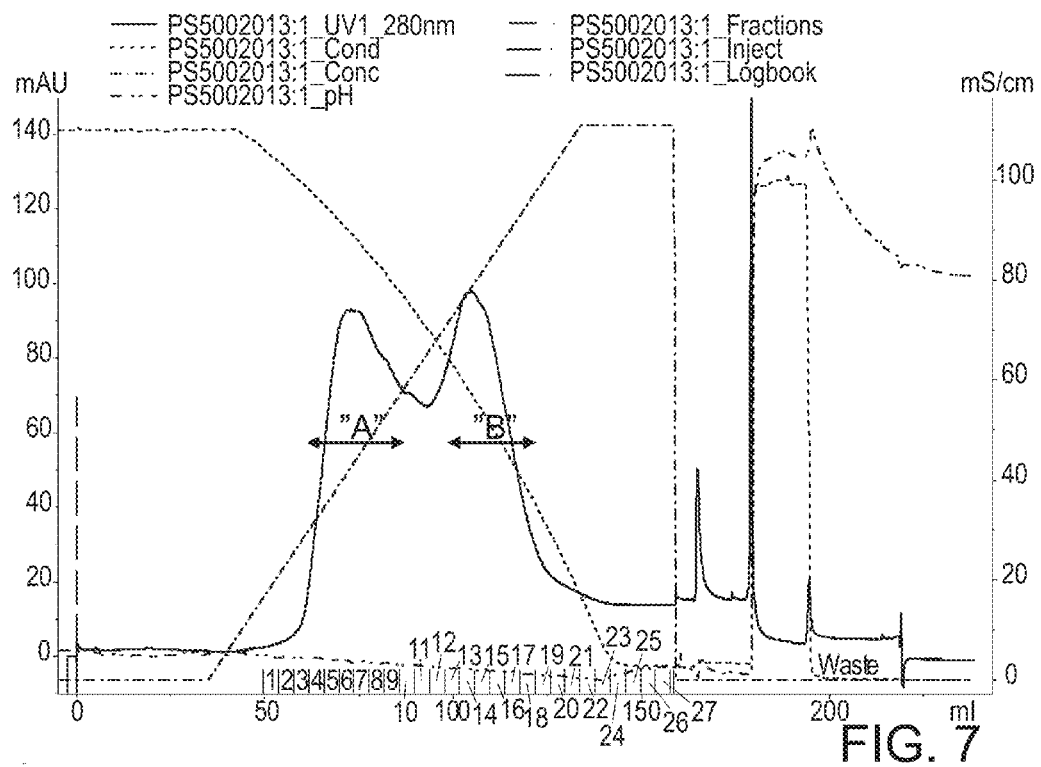
FIG. 7 is a chromatogram from first HIC cycle. Fraction "A" and "B" are indicated by arrows, cf. Example 5.

The FVII eluted in two overlapping major peaks (chromatogram in FIG. 7). Fractions containing the first peak were pooled (fraction "A", FIG. 7) and further purified by a second cycle of HIC, using the same chromatographic procedure as for the first HIC cycle (chromatogram in FIG. 8). Fractions containing the second major peak (fraction "B", FIG. 4) were pooled as well and further purified by a second cycle of HIC, using the same chromatographic procedure as for the first HIC cycle (chromatogram in FIG. 9).

Figure 8:
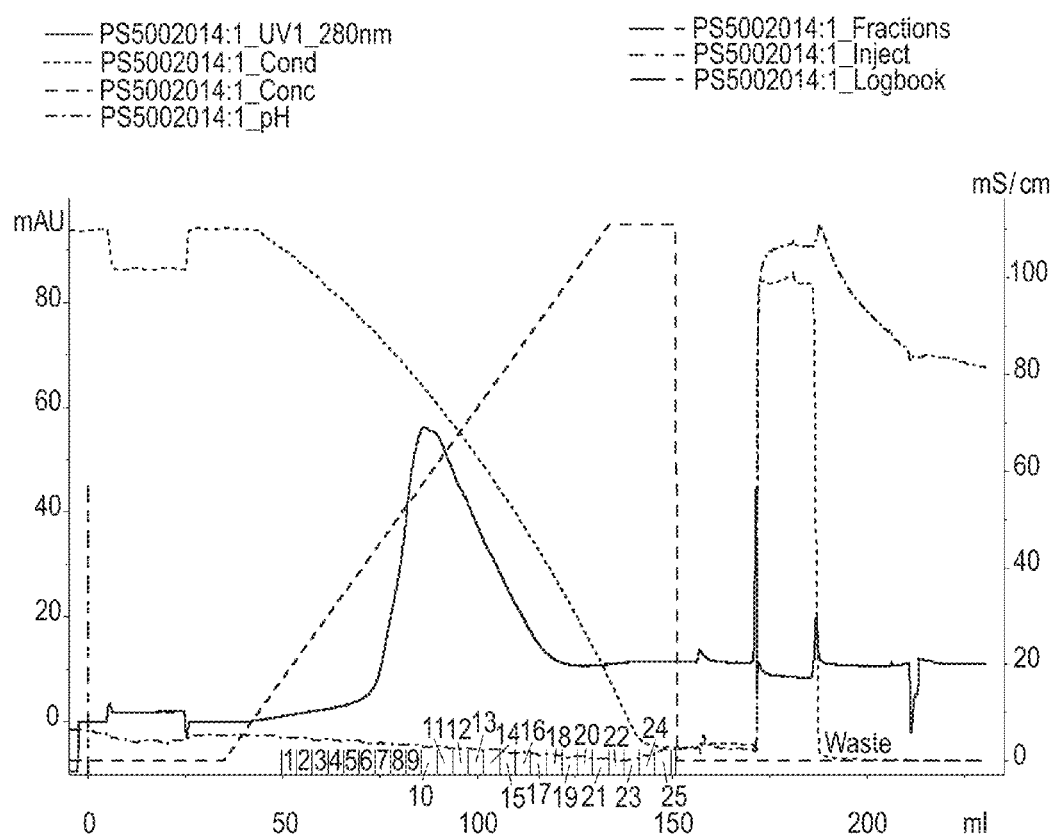
FIG. 8 is a chromatogram obtained by reloading fraction "A" onto the HIC column. Glc-Ser52-FVII was identified in the peak fraction, fraction 10, cf. Example 5.
Figure 10:
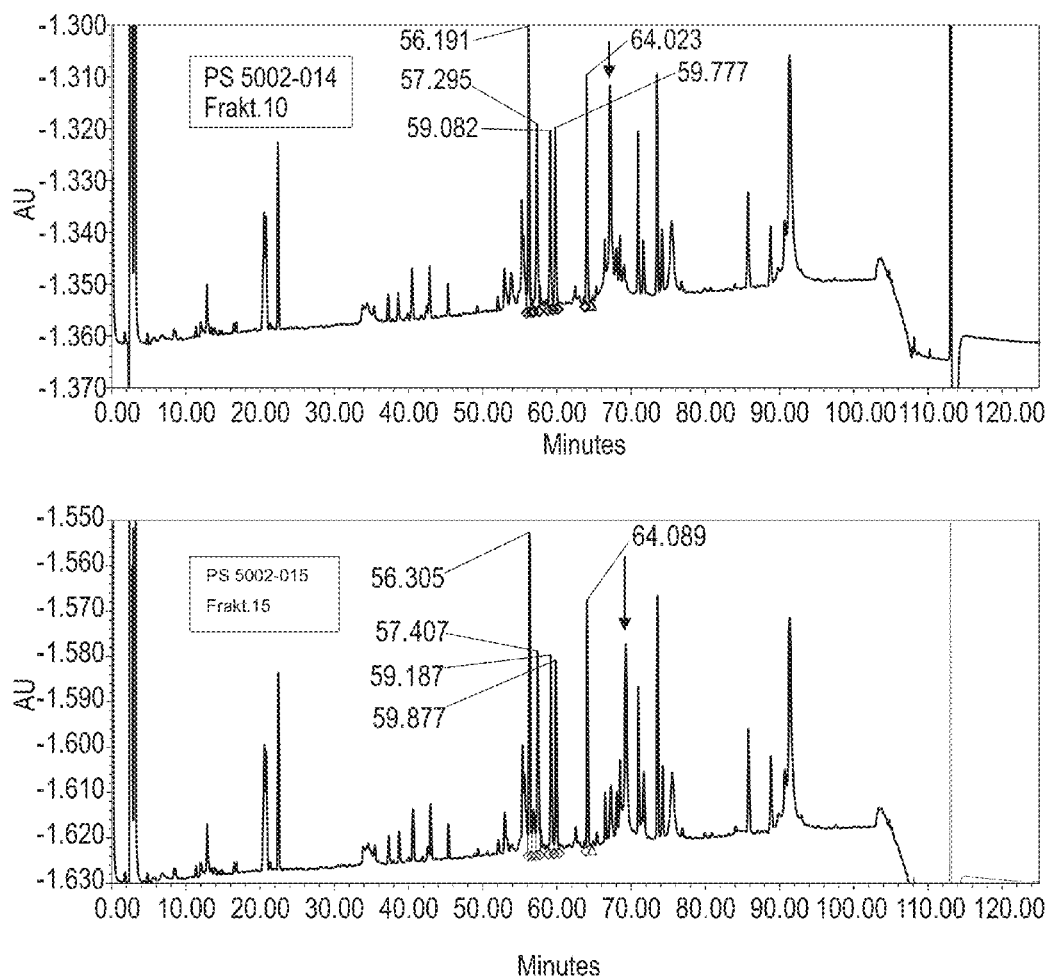
FIG. 10 illustrates a tryptic peptide mapping of rFVIIa as described in General methods of the peak fractions obtained from HIC. Top: Tryptic peptide map of the peak fraction, Fraction 10, the arrow indicate the Glc-O-Ser52 O-glycopeptide. Bottom: Tryptic peptide map of the peak fraction, Fraction 15, the arrow indicate the Xyl-Xyl-Glc-O-Ser52 O-glycopeptide. Other peptide fragments of rFVIIa co-elute with or elute close to the O-glycopeptides, and the content of O-glycopeptides in low amounts can therefore not be determined, cf. Example 5.
Figure 11:
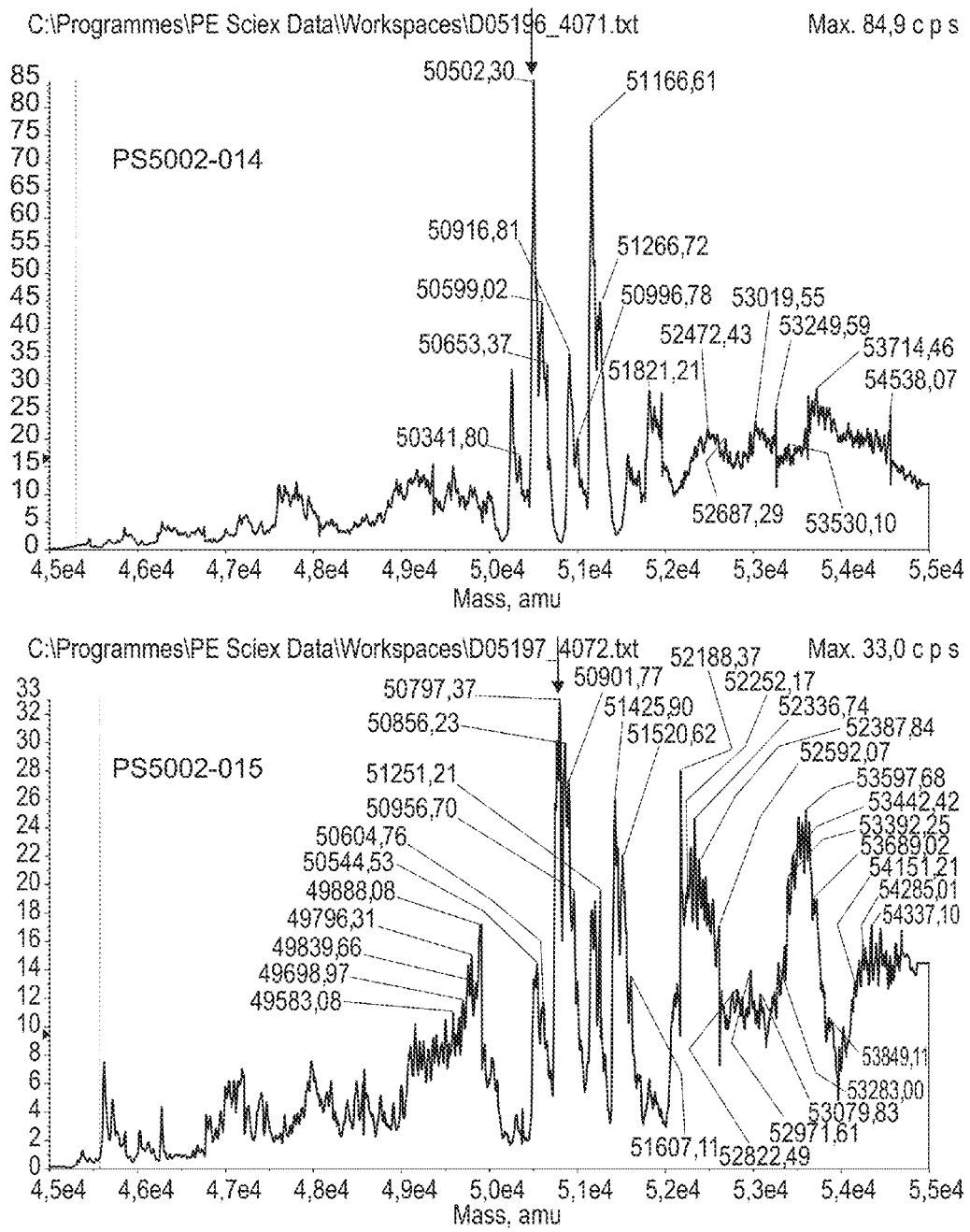
FIG. 11 shows the total mass analysis of rFVIIa as described in General methods of the peak fractions obtained from HIC. Top: Total mass analysis of the peak fraction, Fraction 10, the arrow indicates the Glc-O-Ser52-rFVIIa O-glycoform. Bottom: Total mass analysis of the peak fraction, Fraction 15, the arrow indicates the Xyl-Xyl-Glc-O-rFVIIa O-glycoform. Other O- and/or N-glycoforms of rFVIIa, for example N-glycoforms of rFVIIa lacking one N-acetylneuraminic acid, appear in the mass spectra, and the content of O-glycoforms of rFVIIa in low amounts can therefore not be determined, cf. Example 5.

Purified Glc-O-Ser52-FVII was identified in the peak fraction, fraction 10 (FIG. 8), obtained by reloading fraction "A" onto the second HIC step. Purified Xyl-Xyl-Glc-O-Ser52-FVII was identified in the peak fraction, fraction 15 (FIG. 9), obtained by reloading fraction "B" onto the second HIC step. The identification was obtained by tryptic peptide mapping of rFVIIa as described in General methods (FIGS. 10A and 10B) and by total mass analysis of rFVIIa as described in General methods (FIGS. 11A and 11B). Both analyses showed a high content of Glc-O-Ser52-rFVIIa and a low content of Xyl-Xyl-Glc-O-Ser52-rFVIIa in the peak fraction, Fraction 10, and a low content of Glc-O-Ser52-rFVIIa and a high content of Xyl-Xyl-Glc-O-Ser52-rFVIIa in the peak fraction, Fraction 15. A quantitation of the content of the O-glycoforms in the two peak fractions could not be obtained due to relatively low rFVIIa content in the fractions (FIGS. 10A and 10B) (FIGS. 8A and 8B).

The specific activities of the peak fractions obtained from the HIC (Table 4) were determined by the 1st generation clotting assay. It was found that the Glc-O-Ser52-rFVIIa O-glycoform had a low specific activity while the Xyl-Xyl-Glc-O-Ser52-rFVIIa O-glycoform had a high specific activity.

TABLE 4

Specific activities determined using the 1st generation clotting assay for the peak fractions obtained from HIC. The content of rFVIIa was determined by HPLC.

| Sample | Specific activity |
| --- | --- |
| PS5002-014 Frak. 10 | 44 IU/µg |
| PS5002-015 Frak. 15 | 61 IU/µg |
| PS5002-014/015 starting material | 53 IU/µg |

Example 6

Figure 12:
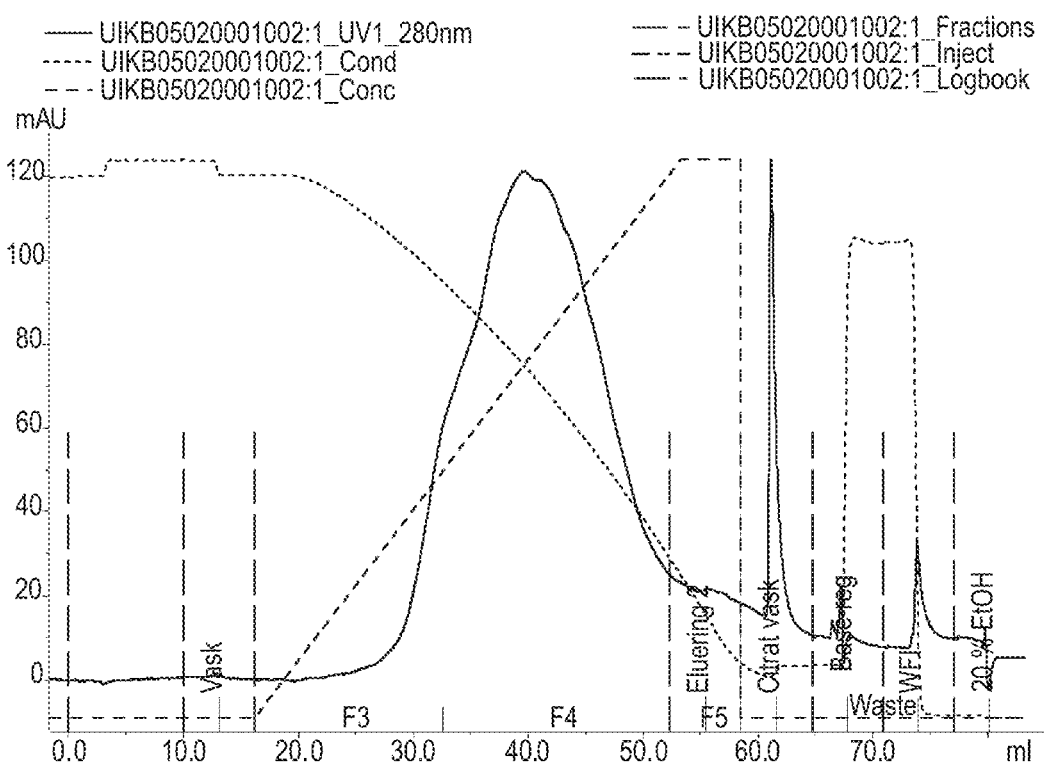
FIG. 12 is a chromatogram of rhFVII separation on TSK-Gel phenyl 5PW, cf. Example 6.

Reduction of GD-FVII by HIC Purification of FVIIa Analogue at pH 6 Using TSK Phenyl 5PW 6 mg of recombinant hFVIIa was added $NH_4$-acetate to a final concentration of 1.8 M and $CaCl_2$ to a final concentration of 10 mM. pH was adjusted to pH 6.0. This sample was added to a column (0.5 cm in inner diameter×10.5 cm length=2 ml column volume (CV)) packed with Toso Haas TSK-Gel phenyl 5 PW, equilibrated with 5 CV 1.8 M $NH_4$-acetate, 10 mM $CaCl_2$, pH 6.0 (load 1.6 g/L). The column was washed with 3 CV 1.8 M $NH_4$-acetate, 10 mM $CaCl_2$, pH 6.0. Elution was performed using a 18 CV linear gradient from 1.8 M $NH_4$-acetate to 50 mM $NH_4$-acetate in a buffer containing 10 mM $CaCl_2$ at pH 6.0. Three samples were collected; the leading edge, the main peak, and the trailing edge. The main peak was collected through peak collection at approximately 50% of maximum absorbance (at 280 nm) on the leading edge and at approximately 20% of maximum absorbance on the trailing edge. Chromatogram in FIG. 12.

The purification was performed at a flow rate of 6-12 CV/h and at a temperature of 5° C. The column was regenerated using 5 CV of 50 mM citrate, pH 7.0 and 5 CV of 0.5 M NaOH.

Figure 13:
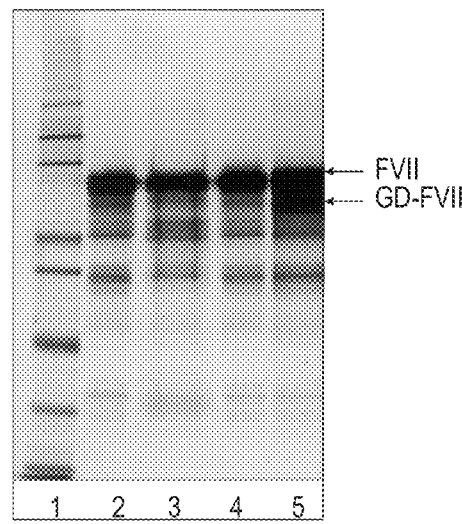
FIG. 13 is an SDS-PAGE gel illustrating the partial removal of GD-FVII. Lane 1: mw standard, lane 2: load sample, lane 3: leading edge, lane 4: main peak, lane 5: trailing edge, cf. Example 6.

The relative content of GD-FVII, mw app. 43 kDA, compared to FVII, mw app. 48 kDA, in the three collected samples and in the application sample was analyzed by non-reducing SDS-PAGE, FIG. 13, and scanning of the gel. A reduced amount of GD-FVII in the main peak was seen, as is reflected in Table 5.

TABLE 5

| Sample | Relative content of GD-FVII | Lane in FIG. 13 |
| --- | --- | --- |
| Application | 19% | 2 |
| Leading edge | 18% | 3 |
| Main peak | 15% | 4 |
| Tailing edge | 61% | 5 |

Example 7

Purification of Glc-O-Ser52-FVII and Xyl-Xyl-Glc-O-Ser52-FVII

Figure 9:
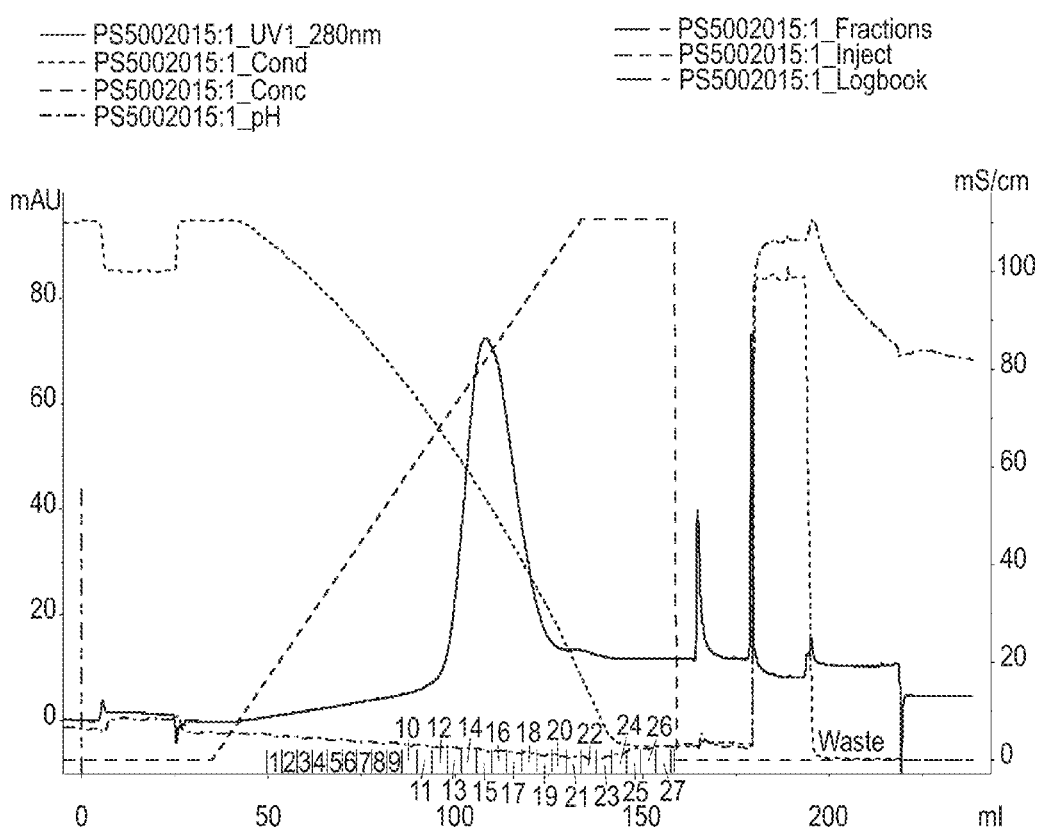
FIG. 9 is a chromatogram obtained by reloading fraction "B" onto the HIC column. Xyl-Xyl-Glc-Ser52-FVII was identified in the peak fraction, fraction 15, cf. Example 5.

Highly purified Glc-O-Ser52-rFVIIa preparation and highly purified Xyl-Xyl-Glc-O-Ser52-rFVIIa preparation were obtained by hydrophobic interaction chromatography. Chromatogram obtained from the second cycle of HIC on the first peak from first cycle of HIC is shown in FIG. 9 and chromatogram obtained from the second cycle of HIC on the second peak from first cycle HIC is shown in FIG. 10. Two pools, Pool A and Pool B, were obtained from the two second cycle HIC runs as indicated in FIGS. 9 and 10. The two pools were concentrated and buffer exchanged into 50 mM $NH_4$-acetate 10 mM $CaCl_2$, pH 6.0 on vivaspin 20 protein concentrators with a 5 kDa molecular weight cut off. Xyl-Xyl-Glc-O-Ser52-rFVIIa and Glc-O-Ser52-rFVIIa in the two concentrated pools were quantified using tryptic peptide mapping as described in Example 7. Concentrated Pool A contained 79% Glc-O-Ser52-rFVIIa and 21% Xyl-Xyl-Glc-O-Ser52-rFVIIa. Concentrated Pool B contained 79% Xyl-Xyl-Glc-O-Ser52-rFVIIa and 21% Glc-O-Ser52-rFVIIa. Specific activity in concentrated Pool A and concentrated Pool B was determined as well, see Table 6.

TABLE 6

Specific activities determined using the 1st generation clotting assay for the peak fractions obtained from HIC. The content of rFVIIa was determined by HPLC.

| Sample | Specific activity |
| --- | --- |
| Concentrated pool A | 35.6 IU/µg |
| Concentrated pool B | 55.5 IU/µg |

Example 8

Reduction of Late Eluting Peaks and Other Product Related Impurities by HIC Purification of FVIIa Using TSK Phenyl 5PW at 20° C.

Six mg of recombinant hFVIIa was added NH$_4$-acetate to a final concentration of 1.8 M and CaCl2 to a final concentration of 10 mM. pH was adjusted to pH 6.0. This sample was added to a column (0.5 cm in inner diameter×10.0 cm length=2 ml column volume (CV)) packed with Toso Haas TSK-Gel phenyl 5 PW, equilibrated with 5 CV 1.8 M NH$_4$-acetate, 10 mM CaCl$_2$, pH 6.0.

The column was washed with 3 CV 1.8 M NH$_4$-acetate, 10 mM CaCl$_2$, pH 6.0. Elution was performed using a 18 CV linear gradient from 1.8 M NH4-acetate to 50 mM NH4-acetate in a buffer containing 10 mM CaCl2, at pH 6.0.

Figure 16:
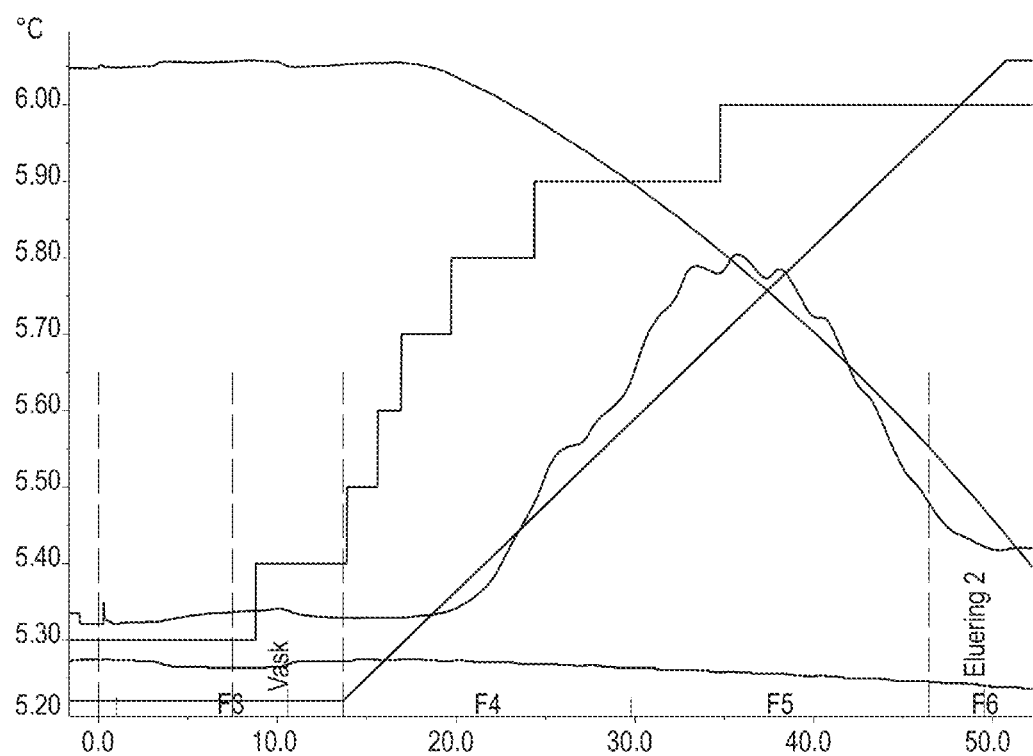
FIG. 16 illustrates the reduction of Late eluting peaks and other product related impurities by HIC purification of FVIIa using TSK Phenyl 5PW at 20° C.

Though peak collection at approximately 65% of maximum absorbance (at 280 nm) on the leading edge and at approximately 20% of maximum absorbance on the trailing edge. A pool was collected, chromatogram in FIG. 16.

The purification was performed at a flow rate between 6 and 12 CV/h and at a temperature of 20° C. The column was regenerated with 50 mM citrate, pH 7.0 and 0.5 M NaOH.

Content of oxidized- and heavy chain degraded FVII and of late eluting peaks was reduced as shown in Table 7.

TABLE 7

| Sample | Oxidized FVII | Heavy chain degraded FVII | Late eluting peaks |
|---|---|---|---|
| Application | 3.9% | 4.9% | 2.7% |
| Pool | 2.3% | 4.5% | 0.5% |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

The invention claimed is:

1. A process for reducing the content of forms of activated Factor VII lacking one or more N-linked glycan(s) in a drug substance of a recombinantly made activated Factor VII polypeptide, said process comprising the steps of:
(a) contacting the drug substance with a hydrophobic interaction chromatography material comprising a butyl ligand and/or phenyl ligand under conditions which facilitate binding of a portion of said drug substance to said hydrophobic interaction chromatography material, said drug substance further comprising a salt selected from: ammonium acetate, ammonium sulphate, ammonium chloride, sodium chloride, sodium acetate, sodium sulphate, potassium acetate, potassium chloride, and potassium sulphate, and/or a zwitterion selected from: glycine, alanine, beta-alanine, leucine, and isoleucine, in a concentration of about 0.0 to 0.1 M or in the range of from 0.5 M to 85% of the saturation concentration for the respective salt at the temperature at which step (a) is carried out;
(b) optionally washing said hydrophobic interaction chromatography material with a washing buffer; and
(c) eluting said hydrophobic interaction chromatography material with an elution buffer, and collecting a purified drug substance of the activated Factor VII polypeptide as an eluate;
wherein the content of forms of activated Factor VII polypeptide lacking one or more N-linked glycan(s) in the purified drug substance collected in step (c) is reduced by at least 50% (w/w) as compared to the drug substance applied in step (a).

2. The process according to claim 1, wherein the load of the drug substance in step (a) is in the range of at least 250 mg recombinant activated Factor VII polypeptide per L resin.

3. The process according to claim 1, wherein the drug substance in step (a) is in liquid form and has an ionic strength of at least 50 mS/cm.

4. The process according to claim 1, wherein the washing buffer in step (b) comprises a salt in a concentration of about 0.7 to about −2.2 M.

5. The process according to claim 1, wherein the elution buffer in step (c) comprises a salt in an initial concentration of about 0.7 to about 2.2 M.

6. The process according to claim 1, wherein the elution buffer in step (c) is a gradient buffer with respect to the salt.

7. The process according claim 6, wherein the initial concentration of the salt of the gradient buffer is in the range of 1.7-2.2 M, and the final concentration of the salt of the gradient buffer is in the range of 0.0-1.6 M.

8. The process according to claim 1, wherein the washing buffer in step (b) comprises a salt selected from: ammonium acetate, ammonium sulfate, ammonium chloride, sodium chloride, sodium acetate, sodium sulphate, potassium acetate, potassium chloride, and potassium sulphate, and/or a zwitterion selected from: glycine, alanine, beta-alanine, leucine, and isoleucine, in a concentration of about 0.0 to 0.1 M or in the range of 0.5 M to 85% of the saturation concentration for the respective salt at the temperature at which step (b) is carried out.

9. The process according to claim 1, wherein the salt is selected from: ammonium acetate, ammonium sulphate, sodium chloride, and sodium acetate.

10. A process for the purification of a drug substance of a recombinant activated Factor VII polypeptide, said drug substance comprising at least 3% of late eluting peaks, wherein the at least 3% of late eluting peaks include forms of activated Factor VII lacking one or more N-linked glycan(s), said process comprising the steps of:
(a) contacting a drug substance comprising a recombinant activated Factor VII polypeptide with a hydrophobic interaction chromatography material under conditions which facilitate binding of a portion of said drug substance to said hydrophobic interaction chromatography material, said drug substance comprising an ammonium salt in a concentration of about 1.5 to about −2.5 M;
(b) washing said hydrophobic interaction chromatography material with a washing buffer comprising the ammonium salt in a concentration of in the range of about 1.5 to about −2.5 M; and
(c) eluting said hydrophobic interaction chromatography material with an elution buffer comprising an ammonium salt, said elution buffer being a gradient buffer with respect to the ammonium salt, and collecting a purified drug substance as an eluate,
wherein steps (b) and (c) may be combined; and
wherein the forms of activated Factor VII polypeptide lacking one or more N-linked glycan(s) in the purified drug substance collected in step (c) is reduced by at least 50% (w/w) as compared to the drug substance applied in step (a).

11. The process according to claim 10, wherein the elution buffer in step (c) is a gradient buffer with respect to the ammonium salt, wherein the initial concentration of the ammonium salt of the gradient buffer is in the range of 1.8-2.2 M, and the final concentration of the ammonium salt of the gradient buffer is in the range of 1.2-1.6 M.

12. The process according to claim 10, wherein steps (a)-(c) are carried out at a temperature in the range of 0-25° C., and wherein steps (a)-(c) are carried out at a pH in the range of 6-9.

\* \* \* \* \*

UNITED STATES PATENT AND TRADEMARK OFFICE
CERTIFICATE OF CORRECTION

| | | |
|---|---|---|
| PATENT NO. | : 9,023,992 B2 | Page 1 of 1 |
| APPLICATION NO. | : 12/884927 | |
| DATED | : May 5, 2015 | |
| INVENTOR(S) | : Daniel E. Rasmussen et al. | |

It is certified that error appears in the above-identified patent and that said Letters Patent is hereby corrected as shown below:

On The Title Page, Item (22) should read -- May 3, 2005

Signed and Sealed this
First Day of March, 2016

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 9,023,992 B2 | Page 1 of 1 |
| APPLICATION NO. | : 12/884927 | |
| DATED | : May 5, 2015 | |
| INVENTOR(S) | : Daniel E. Rasmussen et al. | |

It is certified that error appears in the above-identified patent and that said Letters Patent is hereby corrected as shown below:

In the Claims:

At column 30, claim number 4, line number 20, please replace "...0.7 to about - 2.2m..." with "...0.7 to about 2.2m..."

At column 30, claim number 10, line number 59, please replace "...1.5 to about - 2.5m..." with "...1.5 to about 2.5m..."

Signed and Sealed this
Eighth Day of March, 2016

Michelle K. Lee
*Director of the United States Patent and Trademark Office*